(12) United States Patent
Schmelcher et al.

(10) Patent No.: US 12,091,691 B2
(45) Date of Patent: Sep. 17, 2024

(54) CHIMERIC ENDOLYSIN POLYPEPTIDE

(71) Applicant: Micreos Pharmaceuticals AG, Baar (CH)

(72) Inventors: Mathias Schmelcher, Baar (CH); Christian Alexander Röhrig, Baar (CH); Markus Huemer, Baar (CH); Fritz Eichenseher, Baar (CH)

(73) Assignee: Micreos Pharmaceuticals AG, Baar (CH)

( * ) Notice: Subject to any disclaimer, the term of this patent is extended or adjusted under 35 U.S.C. 154(b) by 0 days.

(21) Appl. No.: 18/582,803

(22) Filed: Feb. 21, 2024

(65) Prior Publication Data
US 2024/0279631 A1     Aug. 22, 2024

Related U.S. Application Data

(62) Division of application No. PCT/EP2023/087535, filed on Dec. 22, 2023.

(51) Int. Cl.
  *C12N 9/36* (2006.01)
  *A61K 38/47* (2006.01)

(52) U.S. Cl.
  CPC ............ *C12N 9/2462* (2013.01); *A61K 38/47* (2013.01); *C12Y 302/01017* (2013.01)

(58) Field of Classification Search
  CPC .................................................. C12N 9/2462
  See application file for complete search history.

(56) References Cited

U.S. PATENT DOCUMENTS

2016/0097044 A1     4/2016   Donovan

FOREIGN PATENT DOCUMENTS

| WO | WO2015/179390 A1 | 11/2015 |
| WO | WO2016142445 A2  | 9/2016  |
| WO | WO2017046021 A1  | 3/2017  |
| WO | WO2018/091707 A1 | 5/2018  |
| WO | WO2021213898 A1  | 10/2021 |

OTHER PUBLICATIONS

Haddad Kashani, Hamed, et al. "Recombinant endolysins as potential therapeutics against antibiotic-resistant *Staphylococcus aureus*: current status of research and novel delivery strategies." Clinical microbiology reviews 31.1 (2018): 10-1128.

*Primary Examiner* — Suzanne M Noakes
(74) *Attorney, Agent, or Firm* — N.V. Nederlandsch Octrooibureau

(57) ABSTRACT

The invention relates to the field of medicine, specifically to the field of treatment of conditions associated with *Staphylococcus* infection. The invention relates to a novel endolysin polypeptide specifically targeting a bacterial *Staphylococcus* cell. The invention further relates to said endolysin polypeptide for medical use, preferably for treating an individual suffering from a condition associated with *Staphylococcus* infection.

Figure 1:
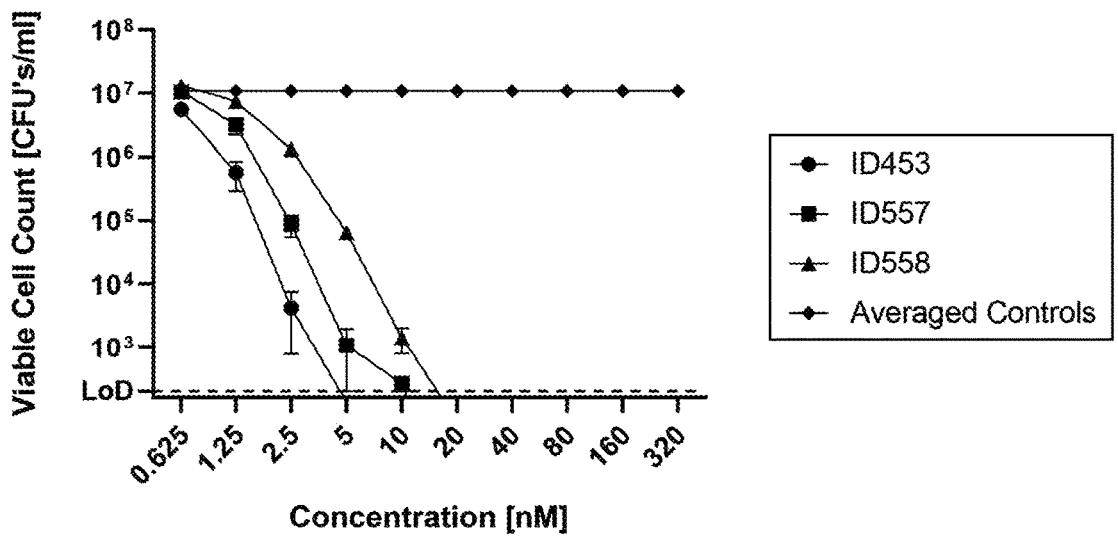

11 Claims, 3 Drawing Sheets
Specification includes a Sequence Listing.

CHIMERIC ENDOLYSIN POLYPEPTIDE

REFERENCE TO AN ELECTRONIC SEQUENCE LISTING

The contents of the electronic sequence listing (P6113465US1 wiposequence St26.xml.; Size: 139 KB; and Date of Creation: Feb. 21, 2024) is herein incorporated by reference in its entirety.

FIELD OF THE INVENTION

The invention relates to the field of medicine, specifically to the field of treatment of conditions associated with *Staphylococcus* infection. The invention relates to a novel endolysin polypeptide specifically targeting a bacterial *Staphylococcus* cell. The invention further relates to said endolysin polypeptide for medical use, preferably for treating an individual suffering from a condition associated with *Staphylococcus* infection.

BACKGROUND OF THE INVENTION

Widespread dissemination of antimicrobial resistance (AMR) genes among pathogenic bacteria has resulted in a health crisis of staggering proportions, with little or no treatment options for those affected and expectations that this problem will become more profound over time. A recent study analyzing the global burden of AMR in 2019 concludes that it has become a leading cause of death, with 1.27 million deaths directly attributable to resistance and many more AMR-associated deaths (ARC., 2022). This is in line with the UK government sponsored Review on Antimicrobial Resistance which estimates that the global death toll caused by AMR could result in an annual 10 million deaths by 2050.

The WHO has identified 6 pathogens causing the majority of fatalities due to resistance: *Escherichia coli*, followed by *Staphylococcus aureus, Klebsiella pneumoniae, Streptococcus pneumoniae, Acinetobacter baumannii*, and *Pseudomonas aeruginosa*. Methicillin resistant *S. aureus* alone was directly responsible for 100,000 deaths in 2019 (ARC., 2022).

Staphylococcal bloodstream infections (SBIs) in particular present an enormous challenge for adequate treatment. Permanent *S. aureus* colonization of the anterior nares in a substantial part of the population (~30%) results in opportunities for the bacteria to enter the bloodstream with potentially devastating consequences. Sepsis and septic shock occur in a significant number of *S. aureus* bloodstream infection cases, but endocarditis and other deep-tissue infections may result (Song et al., 2020). Coagulase negative staphylococci, most notably *S. epidermidis* are also a frequent cause of SBIs. Having fewer virulence genes than *S. aureus*, SBIs caused by *S. epidermidis* generally presents as subacute or chronic but can disseminate to many parts of the body. Biofilm production is a common feature of many *S. epidermidis* strains and colonization of implanted devices such as intravascular devices, cerebrospinal fluid shunts, intraocular lenses, prosthetic joints and heart valve replacements frequently occurs. Treatment of established SBIs requires antimicrobials although removal of affected medical devices is recommended. Methicillin resistance among strains of both bacteria is becoming more prevalent, reducing the number of antibiotic treatments available. Vancomycin and linezolid treatment potentially have serious side effects and cases that display increased minimal inhibitory concentration and even complete resistance to these compounds are becoming more frequent. In fact, multidrug resistance has been observed in 70-85% of nosocomial strains of *S. epidermidis* (Kleinschmidt et al., 2015).

There is therefore an urgent need for novel antimicrobial compounds to combat these infections. Peptidoglycan hydrolases (PGHs) can cleave specific bonds within the peptidoglycan (PG) network of bacteria and have been shown to be active against biofilms. Their high lytic activity makes PGHs potent anti-staphylococcal agents. Endolysins are highly specific, phage-derived PGHs, active against both drug-sensitive and resistant bacteria (Schmelcher et al. 2012). As potential alternatives to antibiotics, they have undergone investigations in vitro, in vivo and are under trial in several clinical studies (Kashani et al. 2017). PGHs of Staphylococci regularly display a domain-like architecture, consisting of enzymatically active domains (EADs) and cell-wall-binding domains (CBDs). The high specificity of staphylococcal PGHs may be attributed to their CBDs, which regularly feature an SH3b-fold. The structures of staphylococcal endolysin SH3b domains have been solved and display great homology to the bacteriocins lysostaphin (LST) and ALE1, suggesting a common recognition site in the PG.

The EADs are more diverse and can be grouped according to their structure and cleavage site within the PG. Cysteine, histidine dependent amidohydrolase/peptidase (CHAP) domains are frequently found in staphylolytic endolysins, for example in phage Twort or phage K (Korndörfer et al. 2006). Depending on the CHAP domain present, cleavage can occur at different locations in the PG, including the amide bond of the sugar backbone to the stem peptide and the link of the stem peptide to the peptide cross bridge. Herein, the amidohydrolase/peptidase activity of a CHAP domain is referred to as CHAP activity. M23 domains, have only been found in one endolysin (phage 2638), but are also present in the staphylococcal bacteriocins LST and its homologue ALE1. The M23 domains of LST and ALE1 cleave the pentaglycine cross-bridge, which connects adjacent stem peptides in the PG of *S. aureus*, whereas the M23 domain of phage 2638 cuts between the peptide bridge and the stem peptide (Gründling et al. 2006; Schmelcher et al. 2015 JAC). Herein, the peptidase activity of an M23 domain is referred to as M23 peptidase activity or M23 activity. Endolysins from phages infecting *Staphylococcus* have been shown to potentially control these pathogens. In most cases, major obstacles in the application of endolysins targeting *Staphylococcus* species are low enzyme activity, difficult production in large quantities and/or protein stability. Accordingly, there is a need for an endolysin polypeptide with improved characteristics on for example antimicrobial activity. Several endolysins have been presented in WO2021/213898. Altogether, especially for systemic infections and sepsis and for prosthetic devices and catheters, there is a need for a single endolysin polypeptide with improved characteristics on antimicrobial activity and stability.

DESCRIPTION OF THE INVENTION

The inventors have established that a combination of an M23 endopeptidase and a CHAP domain on a single chimeric endolysin polypeptide provides desired improved activity.

Accordingly, in a first aspect the invention relates to an endolysin polypeptide that has lytic activity for *Staphylococcus*, said endolysin polypeptide comprising a polypeptide, wherein the amino acid sequence of the polypeptide has at least 93% sequence identity with SEQ ID NO: 1, and wherein the endolysin polypeptide has enhanced lytic activity for *Staphylococcus* in human serum compared to:

the endolysin with the amino acid sequence as set forward in SEQ ID NO: 2, and/or the endolysin with the amino acid sequence as set forward in SEQ ID NO: 3.

The endolysin polypeptide is herein interchangeably referred to as the endolysin polypeptide as disclosed herein, the endolysin as disclosed herein, the endolysin polypeptide and the endolysin. The lytic activity may be determined using any method known to the person skilled in the art.

In the embodiments herein, a method as described in the examples herein is preferably used to determine (enhanced) lytic activity of the endolysin. In the embodiments herein, the lytic activity is preferably determined at 37°. The lytic activity is enhanced when it is at least 1%, 2%, 3%, 4%, 5%, 6%, 7%, 8%, 9%, 10%, 20%, 30%, 40%, 50%, or at least 100% higher as compared to an endolysin with the amino acid sequence as set forward in SEQ ID NO: 2 and/or SEQ ID NO: 3.

In the embodiments herein, the endolysin polypeptide preferably has enhanced lytic activity for both coagulase-positive as coagulase-negative species of *Staphylococcus*, especially for either or both *Staphylococcus aureus* and *Staphylococcus epidermidis*.

In the embodiments herein, the endolysin may comprise a polypeptide, wherein the amino acid sequence of the polypeptide has at least 93%, more preferably 94%, 95%, 96%, 97%, 98%, 99%, or most preferably 100% sequence identity with SEQ ID NO: 1. In the embodiments herein, the amino acid sequence of the endolysin polypeptide may have at least 93%, more preferably at least 94%, 95%, 96%, 97%, 98%, 99%, or most preferably 100% sequence identity with SEQ ID NO: 1.

In the embodiments herein, in the endolysin polypeptide, the M23 endopeptidase domain and the CHAP domain are preferably separated by a linker. In the embodiments herein, said linker may be a peptide comprised of 10, 11, 12, 13, 14, 15, 16, 17, 18, 19, 20, 21, 22, or most preferably at least 23 amino acids. In the embodiments herein, said linker may be a peptide comprised of 10, 11, 12, 13, 14, 15, 16, 17, 18, 19, 20, 21, 22, or most preferably at least 23 amino acids, wherein said peptide has an amino acid sequence that has at least 80%, more preferably 81%, 82%, 83%, 84%, 85%, 86%, 87%, 88%, 89%, 90%, 91%, 92%, 93%, 94%, 95%, 96%, 97%, 98%, 99% or most preferably 100% sequence similarity and/or identity with SEQ ID NO: 8. In the embodiments herein, said linker may be a peptide comprised of 10, 11, 12, 13, 14, 15, 16, 17, 18, 19, 20, 21, 22, or most preferably at least 23 amino acids, wherein said peptide has an amino acid sequence that has at least 80%, more preferably 81%, 82%, 83%, 84%, 85%, 86%, 87%, 88%, 89%, 90%, 91%, 92%, 93%, 94%, 95%, 96%, 97%, 98%, 99% or most preferably 100% sequence similarity with SEQ ID NO: 8. In the embodiments herein, said linker may be a peptide comprised of 10, 11, 12, 13, 14, 15, 16, 17, 18, 19, 20, 21, 22, or most preferably at least 23 amino acids, wherein said peptide has an amino acid sequence that has at least 80%, more preferably 81%, 82%, 83%, 84%, 85%, 86%, 87%, 88%, 89%, 90%, 91%, 92%, 93%, 94%, 95%, 96%, 97%, 98%, 99% or most preferably 100% sequence identity with SEQ ID NO: 8. Preferably, said linker comprises at least 10, 11, 12, 13, 14, 15, 16, 17, 18, 19, 20, 21, 22, or most preferably at least 23 amino acids of SEQ ID NO: 8.

Preferably, said linker comprises or consists of one of the peptides as set forward in Table A.

TABLE A

| preferred linker between the CHAP domain and the M23 domain | |
|---|---|
| Linker | SEQ ID NO: |
| SVKKKDTKKKPKPSNRDGINKDK | 12 |
| VKKKDTKKKPKPSNRDGINKDK | 13 |
| KKKDTKKKPKPSNRDGINKDK | 14 |
| KKDTKKKPKPSNRDGINKDK | 15 |
| KDTKKKPKPSNRDGINKDK | 16 |
| DTKKKPKPSNRDGINKDK | 17 |
| TKKKPKPSNRDGINKDK | 18 |
| KKKPKPSNRDGINKDK | 19 |
| KKPKPSNRDGINKDK | 20 |
| KPKPSNRDGINKDK | 21 |
| PKPSNRDGINKDK | 22 |
| KPSNRDGINKDK | 23 |
| PSNRDGINKDK | 24 |
| SNRDGINKDK | 25 |
| SVKKKDTKKKPKPSNRDGINKD | 26 |
| VKKKDTKKKPKPSNRDGINKD | 27 |
| KKKDTKKKPKPSNRDGINKD | 28 |
| KKDTKKKPKPSNRDGINKD | 29 |
| KDTKKKPKPSNRDGINKD | 30 |
| DTKKKPKPSNRDGINKD | 31 |
| TKKKPKPSNRDGINKD | 32 |
| KKKPKPSNRDGINKD | 33 |
| KKPKPSNRDGINKD | 34 |
| KPKPSNRDGINKD | 35 |
| PKPSNRDGINKD | 36 |
| KPSNRDGINKD | 37 |
| PSNRDGINKD | 38 |
| SVKKKDTKKKPKPSNRDGINK | 39 |
| VKKKDTKKKPKPSNRDGINK | 40 |
| KKKDTKKKPKPSNRDGINK | 41 |
| KKDTKKKPKPSNRDGINK | 42 |
| KDTKKKPKPSNRDGINK | 43 |
| DTKKKPKPSNRDGINK | 44 |
| TKKKPKPSNRDGINK | 45 |
| KKKPKPSNRDGINK | 46 |
| KKPKPSNRDGINK | 47 |

TABLE A-continued preferred linker between the CHAP domain and the M23 domain

| Linker | SEQ ID NO: |
|---|---|
| KPKPSNRDGINK | 48 |
| PKPSNRDGINK | 49 |
| KPSNRDGINK | 50 |
| SVKKKDTKKKPKPSNRDGIN | 51 |
| VKKKDTKKKPKPSNRDGIN | 52 |
| KKKDTKKKPKPSNRDGIN | 53 |
| KKDTKKKPKPSNRDGIN | 54 |
| KDTKKKPKPSNRDGIN | 55 |
| DTKKKPKPSNRDGIN | 56 |
| TKKKPKPSNRDGIN | 57 |
| KKKPKPSNRDGIN | 58 |
| KKPKPSNRDGIN | 59 |
| KPKPSNRDGIN | 60 |
| PKPSNRDGIN | 61 |
| SVKKKDTKKKPKPSNRDGI | 62 |
| VKKKDTKKKPKPSNRDGI | 63 |
| KKKDTKKKPKPSNRDGI | 64 |
| KKDTKKKPKPSNRDGI | 65 |
| KDTKKKPKPSNRDGI | 66 |
| DTKKKPKPSNRDGI | 67 |
| TKKKPKPSNRDGI | 68 |
| KKKPKPSNRDGI | 69 |
| KKPKPSNRDGI | 70 |
| KPKPSNRDGI | 71 |
| SVKKKDTKKKPKPSNRDG | 72 |
| VKKKDTKKKPKPSNRDG | 73 |
| KKKDTKKKPKPSNRDG | 74 |
| KKDTKKKPKPSNRDG | 75 |
| KDTKKKPKPSNRDG | 76 |
| DTKKKPKPSNRDG | 77 |
| TKKKPKPSNRDG | 78 |
| KKKPKPSNRDG | 79 |
| KKPKPSNRDG | 80 |
| SVKKKDTKKKPKPSNRD | 81 |
| VKKKDTKKKPKPSNRD | 82 |
| KKKDTKKKPKPSNRD | 83 |
| KKDTKKKPKPSNRD | 84 |
| KDTKKKPKPSNRD | 85 |
| DTKKKPKPSNRD | 86 |
| TKKKPKPSNRD | 87 |
| KKKPKPSNRD | 88 |
| SVKKKDTKKKPKPSNR | 89 |
| VKKKDTKKKPKPSNR | 90 |
| KKKDTKKKPKPSNR | 91 |
| KKDTKKKPKPSNR | 92 |
| KDTKKKPKPSNR | 93 |
| DTKKKPKPSNR | 94 |
| TKKKPKPSNR | 95 |
| SVKKKDTKKKPKPSN | 96 |
| VKKKDTKKKPKPSN | 97 |
| KKKDTKKKPKPSN | 98 |
| KKDTKKKPKPSN | 99 |
| KDTKKKPKPSN | 100 |
| DTKKKPKPSN | 101 |
| SVKKKDTKKKPKPS | 102 |
| VKKKDTKKKPKPS | 103 |
| KKKDTKKKPKPS | 104 |
| KKDTKKKPKPS | 105 |
| KDTKKKPKPS | 106 |
| SVKKKDTKKKPKP | 107 |
| VKKKDTKKKPKP | 108 |
| KKKDTKKKPKP | 109 |
| KKDTKKKPKP | 110 |
| SVKKKDTKKKPK | 111 |
| VKKKDTKKKPK | 112 |
| KKKDTKKKPK | 113 |
| SVKKKDTKKKP | 114 |
| VKKKDTKKKP | 115 |
| SVKKKDTKKK | 116 |

In the embodiments herein, in the endolysin polypeptide, the M23 domain and the SH3b domain are preferably separated by a linker. In the embodiments herein, said linker may be a peptide comprised of 5, 6, 7, 8, 9, 10, 11, 12, or most preferably at least 13 amino acids. In the embodiments herein, said linker may be a peptide comprised of 5, 6, 7, 8, 9, 10, 11, 12, or most preferably at least 13 amino acids, wherein said peptide has an amino acid sequence that has at least 80%, more preferably 81%, 82%, 83%, 84%, 85%, 86%, 87%, 88%, 89%, 90%, 91%, 92%, 93%, 94%, 95%, 96%, 97%, 98%, 99% or most preferably 100% sequence similarity and/or identity with SEQ ID NO: 9. In the embodiments herein, said linker may be a peptide comprised of 5, 6, 7, 8, 9, 10, 11, 12, or most preferably at least 13 amino acids, wherein said peptide has an amino acid sequence that has at least 80%, more preferably 81%, 82%, 83%, 84%, 85%, 86%, 87%, 88%, 89%, 90%, 91%, 92%, 93%, 94%, 95%, 96%, 97%, 98%, 99% or most preferably 100% sequence similarity with SEQ ID NO: 9. In the embodiments herein, said linker may be a peptide comprised of 5, 6, 7, 8, 9, 10, 11, 12, or most preferably at least 13 amino acids, wherein said peptide has an amino acid sequence that has at least 80%, more preferably 81%, 82%, 83%, 84%, 85%, 86%, 87%, 88%, 89%, 90%, 91%, 92%, 93%, 94%, 95%, 96%, 97%, 98%, 99% or most preferably 100% sequence identity with SEQ ID NO: 9. Preferably, said linker comprises at least 5, 6, 7, 8, 9, 10, 11, 12, or most preferably at least 13 amino acids of SEQ ID NO: 9. Preferably, said linker comprises or consists of one of the peptides as set forward in Table B.

TABLE B

| preferred linker between the M23 domain and the SH3b domain | |
|---|---|
| Linker | SEQ ID NO: |
| KAGGTVTPTPNTG | 117 |
| KAGGTVTPTPNT | 118 |
| KAGGTVTPTPN | 119 |
| KAGGTVTPTP | 120 |
| KAGGTVTPT | 121 |
| KAGGTVTP | 122 |
| KAGGTVT | 123 |
| KAGGTV | 124 |
| KAGGT | 125 |
| AGGTVTPTPNTG | 126 |
| AGGTVTPTPNT | 127 |
| AGGTVTPTPN | 128 |
| AGGTVTPTP | 129 |
| AGGTVTPT | 130 |
| AGGTVTP | 131 |
| AGGTVT | 132 |
| AGGTV | 133 |
| GGTVTPTPNTG | 134 |
| GGTVTPTPNT | 135 |
| GGTVTPTPN | 136 |
| GGTVTPTP | 137 |
| GGTVTPT | 138 |
| GGTVTP | 139 |
| GGTVT | 140 |

TABLE B-continued

| preferred linker between the M23 domain and the SH3b domain | |
|---|---|
| Linker | SEQ ID NO: |
| GTVTPTPNTG | 141 |
| GTVTPTPNT | 142 |
| GTVTPTPN | 143 |
| GTVTPTP | 144 |
| GTVTPT | 145 |
| GTVTP | 146 |
| TVTPTPNTG | 147 |
| TVTPTPNT | 148 |
| TVTPTPN | 149 |
| TVTPTP | 150 |
| TVTPT | 151 |
| VTPTPNTG | 152 |
| VTPTPNT | 153 |
| VTPTPN | 154 |
| VTPTP | 155 |
| TPTPNTG | 156 |
| TPTPNT | 157 |
| TPTPN | 158 |
| PTPNTG | 159 |
| PTPNT | 160 |
| TPNTG | 161 |

Further provided is a polynucleotide encoding an endolysin polypeptide as disclosed herein. Said polynucleotide is herein also referred to as a polynucleotide as disclosed herein. The polynucleotide may be any type of polynucleotide know to the person skilled in the art, such as a DNA, an RNA or an mRNA. The polynucleotide may e.g. be a DNA encoding the endolysin polypeptide which DNA is to be expressed in a host cell or in an in vitro transcription/translation system. The polynucleotide may also be an mRNA to be delivered to a host for in vivo transcription/translation, wherein the host may be a cell or a multicellular organism such as a mammal. Also provided is a nucleic acid construct comprising a polynucleotide as disclosed herein. Said nucleic acid construct is herein referred to as a nucleic acid construct as disclosed herein. Also provided is an expression vector comprising a nucleic acid construct as disclosed herein. Said expression vector is herein referred to as an expression vector as disclosed herein. An expression vector as disclosed herein may be a recombinant expression vector. Such vector may constitute a plasmid, a cosmid, a bacteriophage or a virus, or a part thereof, which is transformed by introducing a nucleic acid construct or a polynucleotide as disclosed herein. Such transformation vectors specific to the host organism to be transformed are well known to those skilled in the art and widely described in the literature. In order to produce a polynucleotide or endolysin polypeptide as disclosed herein in a host, a process for the transformation of a host organism, and integration of a polynucleotide, nucleic acid construct or expression vector as disclosed herein may be appropriate. Such transformation may be carried out by any suitable known means which have been widely described in the specialist literature and are well-known to the person skilled in the art. Also provided is a host cell comprising a polynucleotide as disclosed herein, a nucleic acid construct as disclosed herein or an expression construct as disclosed herein. Said host cell is herein referred to as a host cell as disclosed herein. A host cell as disclosed herein may be any microbial, prokaryotic or eukaryotic, cell which is suitable for expression of the endolysin polypeptide as disclosed herein. Preferably, said cell is an *E. coli*, such as *E. coli* XL1blue MRF, *E. coli* BL21(DE3).

Further provided is a method for the production of an endolysin polypeptide as disclosed herein comprising:
 culturing a host cell as disclosed herein under conditions conducive to the production of the endolysin polypeptide,
 optionally isolating and purifying the endolysin polypeptide from the culture broth, and
 optionally freeze-drying or spray-drying the endolysin polypeptide.

Preferably, an *E. coli* is used in the method for producing an endolysin polypeptide as disclosed herein. Preferably, an *E. coli* XL1blue MRF or *E. coli* BL21-Gold(DE3) is used in step i). Preferably, when a His-tag is used, in the step of isolation and purification, IMAC and Econo-Pac Chromatography columns (Biorad) packed with 5 mL low density Nickel chelating agarose beads (ABT beads) in combination with gravity flow can be used to purify an endolysin polypeptide as disclosed herein. The eluted polypeptide can be dialyzed for 2, 4, and 12 hours against 3×1 l lyophilization buffer, said buffer preferably comprising 50 mM phosphate, 500 mM sucrose, 200 mM mannitol, 0.005% polysorbate 20, pH 7.4.

In an embodiment, no His-tag is used; preferably no tag at all is used; accordingly, in an embodiment, the endolysin polypeptide comprises no His-tag or comprises no tag.

Lyophilisation and reconstitution are preferably construed as dehydration by freeze-drying or spray-drying and subsequent reconstitution of the sample by adding water. Preferably, lyophilisation and reconstitution is performed by dialyzing against 3 changes of 300 ml lyophilization buffer (50 mM phosphate or Tris, 500 mM sucrose, 200 mM mannitol, pH 7.4) aliquot and freezing in the gaseous phase of liquid nitrogen. Freeze-drying is preferably performed under standard conditions, preferably at −40° C. and vacuum at 75 mTorr for 60 minutes, followed by increasing the temperature during 5 hours to −10° C. and another 60 minutes at −10° C. at the same vacuum levels. As a final step, the temperature is preferably increased to 25° C. during 10 hours. Spray-drying may be performed using any method known to the person skilled in the art. The endolysin polypeptide is preferably reconstituted by the addition of water.

Further provided is a method for purifying an endolysin polypeptide as disclosed herein with enhanced activity comprising dialysis of an endolysin polypeptide as disclosed herein, said dialysis comprising the steps of:
 i) dialysis against a buffer comprising a chelating compound, and
 ii) dialysis against a divalent metal ion-containing buffer, preferably a divalent metal ion selected from the group consisting of $Co^{2+}$, $Cu^{2+}$, $Mg^{2+}$, $Ca^{2+}$, $Mn^{2+}$ and $Zn^{2+}$.

A "chelating compound" is defined herein as a compound that binds a metal ion. Well known chelating compounds are ethylenediaminetetraacetic acid (EDTA) and ethylene glycol tetraacetic acid (EGTA). Preferably EDTA is used in step i) of the method for purifying.

Preferably, the divalent metal ion of step ii) is selected from the group consisting $Mn^{2+}$, $Co^{2+}$, $Cu^{2+}$, more preferably, said divalent metal ion is selected from the group consisting of $Mn^{2+}$ and $Co^{2+}$, even more preferably said divalent metal ion is $Mn^{2+}$.

It has been demonstrated previously that substituting a divalent metal ion by any of the above defined resulted in an increase of a lytic activity of Ply2638 of 2-2.5 fold. Lytic activity was assessed as described in the examples herein. Preferably, the method leads to an increase in a lytic activity of at least 1.1, 1.2, 1.3, 1.4, 1.5, 1.6, 1.7, 1.8, 1.9 or 2 fold as compared to an untreated polypeptide. Even more preferably, the method leads to an increase in a lytic activity of at least 2.5 fold.

Further provided is a composition comprising an endolysin polypeptide as disclosed herein or a polynucleotide as disclosed herein, or a nucleic acid construct as disclosed herein, or an expression construct as disclosed herein, or a host cell as disclosed herein. Such composition as disclosed herein may comprise a mixture of different polynucleotides, and/or nucleic acid constructs and/or endolysin polypeptides and/or vectors and/or cells as disclosed herein or as obtainable by a method as disclosed herein. Said composition is herein also referred to as a composition as disclosed herein.

In the embodiments herein, the composition may further comprise an excipient acceptable for cosmetics, i.e. an excipient acceptable for cosmetic use. Such excipient acceptable for cosmetics may be any excipient acceptable for cosmetics known to the person skilled in the art, such as but not limited to an emulsifying agent, an emollient, a dye, a colorant, a binder, an anti-foaming agent, a surfactant, a preservative and a film forming agent.

A composition as disclosed herein may further comprise a pharmaceutically acceptable excipient. Such composition is herein referred to as a pharmaceutical composition and is preferably for use as a medicine or as a medicament. Preferably the medicament is used in the treatment of infectious diseases, preferably infection with a *Staphylococcus* such as *Staphylococcus aureus* and *Staphylococcus epidermidis*.

Accordingly, further provided is a pharmaceutical composition comprising an endolysin polypeptide as disclosed herein, a polynucleotide as disclosed herein, a nucleic acid construct as disclosed herein, an expression construct as disclosed herein, and/or a host cell as disclosed herein; said pharmaceutical composition further comprising a pharmaceutically acceptable excipient.

A composition or a pharmaceutical composition as disclosed herein may further comprise one or more additional active ingredients. Active is preferably defined as showing a lytic activity as defined elsewhere herein. Preferably, said one or more additional active ingredients are selected from the group consisting of a bacteriophage or phage, a phage endolysin derived from such phage and an antibiotic. A phage encompassed herein can be any phage known in literature. Preferably, such phage is, but is not limited, from a family of the list consisting of Myoviridae, Siphoviridae and Podoviridae. Such phage may also be from a family of the list consisting of Tectiviridae, Corticoviridae, Lipothrixviridae, Plasmaviridae, Rudiviridae, Fuselloviridae, Inoviridae, Microviridae, Leviviridae and Cystoviridae. Within the context of the invention, a combination of active ingredients as defined herein can be administered sequentially or simultaneously. A composition as defined herein may be in the liquid, solid or semi-liquid or semi-solid form.

A composition of a pharmaceutical composition as disclosed herein may be used to treat animals, including humans, infected with *Staphylococcus* species as defined herein. Any suitable route of administration can be used to administer said composition including but not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges.

A composition or pharmaceutical composition as disclosed is preferably said to be active, functional or therapeutically active or able to treat, prevent and/or delay an infectious disease when it decreases the amount of a *Staphylococcus* species present in a patient or in a cell of said patient or in a cell line or in a cell free in vitro system and preferably means that 99%, 90%, 80%, 70%, 60%, 50%, 40%, 30%, 20%, 10%, 5% or less of the initial amount of a *Staphylococcus* species, is still detectable after treatment. Preferably no *Staphylococcus* species is detectable after treatment. Herein, the expression "amount of *Staphylococcus* species" preferably means alive *Staphylococcus* species. *Staphylococcus* species may be detected using standard techniques known by the artisan such as immunohistochemical techniques using *Staphylococcus* specific antibodies, tube coagulase tests that detect staphylocoagulase or "free coagulase", detection of surface proteins such as clumping factor (slide coagulase test) and/or protein A (commercial latex tests). Alive *Staphylococcus* species may be detected using standard techniques known by the artisan such as microbiological bacterial culture techniques and/or real-time quantitative reverse transcription polymerase chain reaction to assay for bacterial mRNA. Said decrease is preferably assessed in a tissue or in a cell of an individual or a patient by comparison to the amount present in said individual or patient before treatment with the composition or pharmaceutical composition as disclosed herein. Alternatively, the comparison can be made with a tissue or cell of said individual or patient which has not yet been treated with the composition or pharmaceutical composition as disclosed herein in case the treatment is local.

A composition or pharmaceutical composition as disclosed herein may be administered to a subject in need thereof or to a cell, tissue or organ or said patient for at least one day, one week, one month, six months, one year or more.

Accordingly, there is provided a composition or a pharmaceutical composition as disclosed herein, for use as a medicament for the treatment of a subject in need thereof. Preferably, the composition or pharmaceutical composition is used as a medicament in the prevention, delay or treatment of a condition in a subject, wherein the condition is associated with infection with a *Staphylococcus*, such as a coagulase positive- or coagulase-negative *Staphylococcus*, preferably *Staphylococcus aureus* and/or *Staphylococcus epidermidis*. Such condition may be a skin infection, soft tissue infections such as infected diabetic foot ulcers, mastitis, pneumonia, meningitis, endocarditis, Toxic Shock Syndrome (TSS), sepsis, septicaemia, bacteraemia, or osteomyelitis. A skin infection may be one selected from the group consisting of pimples, impetigo, boils, furuncles, cellulitis, folliculitis, carbuncles, scaled skin syndrome, atopic dermatitis, and abscesses.

Further provided is the composition or a pharmaceutical composition as disclosed herein for use as a medicament, wherein the composition or pharmaceutical composition is for systemic or local administration to the subject.

Further provided is the composition or a pharmaceutical composition as disclosed herein for use as a medicament, wherein the condition is selected from the group consisting of bacteraemia, infective endocarditis, prosthetic joint infection, osteomyelitis, indwelling medical device infection and implanted medical device infection.

Further provided is the composition or a pharmaceutical composition as disclosed herein for use as a medicament, wherein the composition or pharmaceutical composition is for systemic or local administration to the subject and wherein the condition is selected from the group consisting of bacteraemia, infective endocarditis, prosthetic joint infection, osteomyelitis, indwelling medical device infection and implanted medical device infection.

Local administration may e.g. be used during surgery, locally at the site of infection or site of implant. The medical use disclosed herein may be formulated as a product as disclosed herein for use as a medicament for treatment of the stated conditions but can equally be formulated as a method of treatment of the stated conditions using a product as disclosed herein, a product as disclosed herein for use in the preparation of a medicament to treat the stated conditions and use of a product as disclosed herein for the treatment of the stated conditions. Such medical uses are all envisaged by the present invention. The subject in need of treatment, delay and/or prevention of the listed conditions may by any animal subject, preferably a mammal, more preferably cattle, domestic animals like a dog or a cat, or a human subject.

Further provided is a method of cosmetic treatment of the skin of a subject comprising administration, to the skin of the subject, of an endolysin polypeptide as disclosed herein, a polynucleotide encoding such endolysin polypeptide or a composition as disclosed herein. The subject may be any animal subject, preferably a mammal, more preferably cattle, domestic animals like a dog or a cat, or a human subject.

Further provided is the in vitro use of an endolysin polypeptide as disclosed herein or a nucleic acid construct as disclosed herein, or an expression construct as disclosed herein, or a host cell as disclosed herein, or a composition or pharmaceutical composition as disclosed herein, as an antimicrobial, preferably as a food additive or as a disinfectant, preferably for coating or impregnating a medical device. Examples of such use are, but are not limited to, rinsing the cups of a milking device with a composition according to the invention before milking to prevent transmission of Staphylococci from cow to cow, cleaning of surfaces in food industry and cleaning chirurgical tools such as asgastrocameras, peritoneoscopes, thoracoscopes and arthoroscopes and medical supplies like catheters and tubes that have long ducts or hollow portions and tend to be repetitively employed by being introduced into the human or animal body. Such use can be combined with any sterilization method or disinfectant known in the art such as ultrasonic cleaning, irradiation or thermal sterilization, by immersing the equipment in a disinfectant solution such as ethanol, ammonium, iodine and/or aldehyde disinfectant, or by using gas sterilization by retaining the device in a closed atmosphere such as formalin gas or ethylene oxide gas.

Further provided is an in vitro method for coating or impregnating a medical device with an endolysin polypeptide as disclosed herein or a composition or a pharmaceutical composition as disclosed herein, comprising contacting the medical device with an endolysin polypeptide as disclosed herein or a composition or pharmaceutical composition as disclosed herein.

Further provided is the use of a an endolysin polypeptide as disclosed herein or a polynucleotide as disclosed herein, or a nucleic acid construct as disclosed herein, or an expression construct as disclosed herein, or a host cell as disclosed herein, or a composition or pharmaceutical composition as disclosed herein, for detecting a *Staphylococcus*, such as *Staphylococcus aureus*, in an ex vivo diagnostic application.

Definitions

"Sequence identity" is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. "Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, MD 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, WI. The aforementioned parameters are the default parameters for amino acid comparisons (along with no penalty for end gaps). Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons. Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A "nucleic acid molecule" or "polynucleotide" (the terms are used interchangeably herein) is represented by a nucleotide sequence. A "polypeptide" is represented by an amino acid sequence. A "nucleic acid construct" is defined as a nucleic acid molecule which is isolated from a naturally occurring gene or which has been modified to contain segments of nucleic acids which are combined or juxtaposed in a manner which would not otherwise exist in nature. A nucleic acid molecule is represented by a nucleotide sequence. Optionally, a nucleotide sequence present in a nucleic acid construct is operably linked to one or more control sequences, which direct the production or expression of said peptide or polypeptide in a cell or in a subject.

"Operably linked" is defined herein as a configuration in which a control sequence is appropriately placed at a position relative to the nucleotide sequence coding for the polypeptide of the invention such that the control sequence directs the production/expression of the peptide or polypeptide of the invention in a cell and/or in a subject. "Operably linked" may also be used for defining a configuration in which a sequence is appropriately placed at a position relative to another sequence coding for a functional domain such that a chimeric polypeptide is encoded in a cell and/or in a subject.

"Expression" is construed as to include any step involved in the production of the peptide or polypeptide including, but not limited to, transcription, post-transcriptional modification, translation, post-translational modification and secretion.

A "control sequence" is defined herein to include all components which are necessary or advantageous for the expression of a polypeptide. At a minimum, the control sequences include a promoter and transcriptional and translational stop signals. Optionally, a promoter represented by a nucleotide sequence present in a nucleic acid construct is operably linked to another nucleotide sequence encoding a peptide or polypeptide as identified herein.

The term "transformation" refers to a permanent or transient genetic change induced in a cell following the incorporation of new DNA (i.e. DNA exogenous to the cell). When the cell is a bacterial cell, as is intended in the present invention, the term usually refers to an extrachromosomal, self-replicating vector which harbors a selectable antibiotic resistance.

An "expression vector" may be any vector which can be conveniently subjected to recombinant DNA procedures and can bring about the expression of a nucleotide sequence encoding a polypeptide of the invention in a cell and/or in a subject. As used herein, the term "promoter" refers to a nucleic acid fragment that functions to control the transcription of one or more genes or nucleic acids, located upstream with respect to the direction of transcription of the transcription initiation site of the gene. It is related to the binding site identified by the presence of a binding site for DNA-dependent RNA polymerase, transcription initiation sites, and any other DNA sequences, including, but not limited to, transcription factor binding sites, repressor and activator protein binding sites, and any other sequences of nucleotides known to one skilled in the art to act directly or indirectly to regulate the amount of transcription from the promoter. Within the context of the invention, a promoter preferably ends at nucleotide −1 of the transcription start site (TSS).

A "polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

The sequence information as provided herein should not be so narrowly construed as to require inclusion of erroneously identified bases. The skilled person is capable of identifying such erroneously identified bases and knows how to correct for such errors.

In addition, it is known to the person skilled in the art that, when expressing proteins, terminal amino acids such as an N-terminal Methionine are sometimes cleaved off.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a nucleic acid molecule or a peptide or polypeptide of a nucleic acid construct or vector or cell as defined herein may comprise additional component(s) than the ones specifically identified; said additional component(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 10% of the value.

All patent and literature references cited in the present specification are hereby incorporated by reference in their entirety.

The examples herein are offered for illustrative purposes only, and are not intended to limit the scope of the present invention in any way.

FIGURE LEGENDS

FIG. 1. Killing of *S. aureus* NR-46543/USA300 JE2 (MRSA) in human serum by peptidoglycan hydrolases.

Quantitative killing assays (QKAs) were performed for peptidoglycan hydrolase (PGH) constructs ID453, ID557, ID558 in human serum against methicillin-resistant *Staphylococcus aureus* (MRSA) NR-46543/USA300 JE2 at 37° C. for 30 min at 180 rpm (25 mm orbit). Viable cell counts (CFUs/ml) (y-axis) of *S. aureus* NR-46543/USA300 JE2 are shown for three PGH constructs in a 2-fold concentration range (x-axis) in nM (320-0.625 nM). The depicted negative control (no addition of PGH) corresponds to the averaged individual controls of the three tested constructs. The limit of detection (LoD) is 200 CFUs/ml (grey dashed line). The y-axis is cut at 160 CFU's/ml. Three biological replicates (n=3) were made. Error bars of averaged controls and constructs represent the standard error of the mean (S.E.M).

Figure 2:
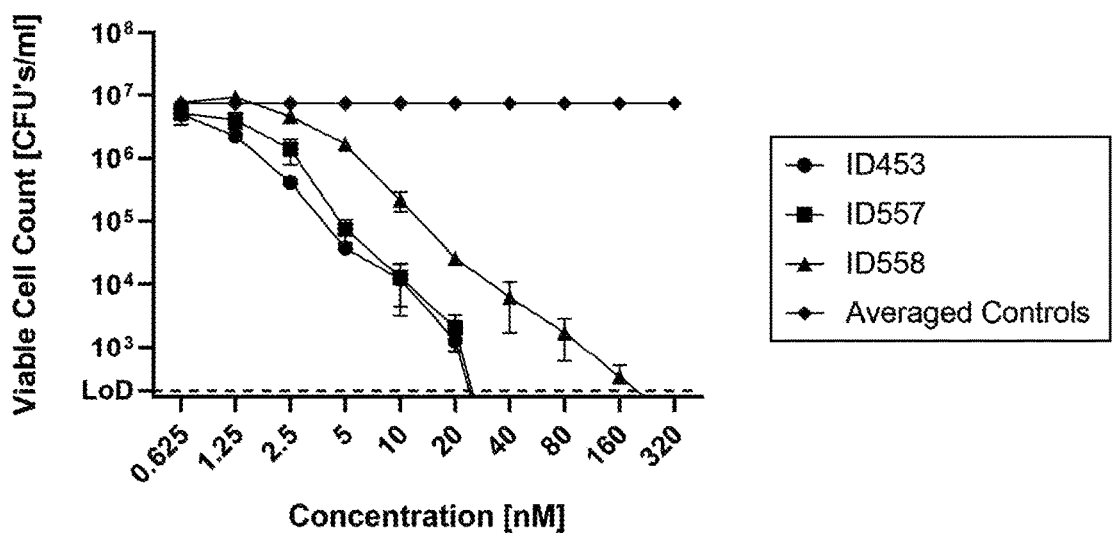

FIG. 2. Killing of *S. aureus* ATCC 12600 (MSSA) in human serum by peptidoglycan hydrolases.

Quantitative killing assays (QKAs) were performed for peptidoglycan hydrolase (PGH) constructs ID453, ID557, ID558 in human serum against methicillin-sensitive *Staphylococcus aureus* (MSSA) ATCC 12600 at 37° C. for 30 min at 180 rpm (25 mm orbit). Viable cell counts (CFUs/ml) (y-axis) of *S. aureus* ATCC 12600 are shown for three PGH constructs in a 2-fold concentration range (x-axis) in nM (320 nM-0.625 nM). The depicted negative control (no addition of PGH) corresponds to the averaged individual controls of the three tested constructs. The limit of detection (LoD) is 200 CFUs/ml (grey dashed line). The y-axis is cut at 160 CFU's/ml. Three biological replicates (n=3) were made. Error bars of averaged controls and constructs represent the standard error of the mean (S.E.M).

Figure 3:
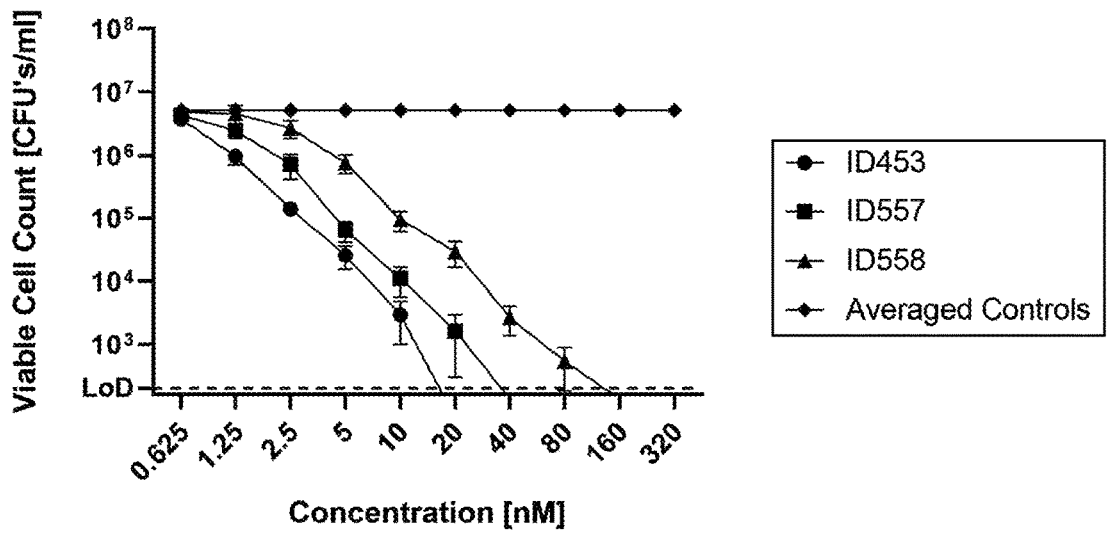

FIG. 3. Killing of *S. aureus* ATCC 12598 (MSSA) in human serum by peptidoglycan hydrolases.

Quantitative killing assays (QKAs) were performed for peptidoglycan hydrolase (PGH) constructs ID453, ID557, ID558 in human serum against methicillin-sensitive *Staphylococcus aureus* (MSSA) ATCC 12598 (Cowan I) at 37° C. for 30 min at 180 rpm (25 mm orbit). Viable cell counts (CFUs/ml) (y-axis) of *S. aureus* ATCC 12598 are shown for three PGH constructs in a 2-fold concentration range (x-axis) in nM (320 nM-0.625 nM). The depicted negative control (no addition of PGH) corresponds to the averaged individual controls of the three tested constructs. The limit of detection (LoD) is 200 CFUs/ml (grey dashed line). The y-axis is cut at 160 CFU's/ml. Three biological replicates (n=3) were made. Error bars of averaged controls and constructs represent the standard error of the mean (S.E.M).

Figure 4:
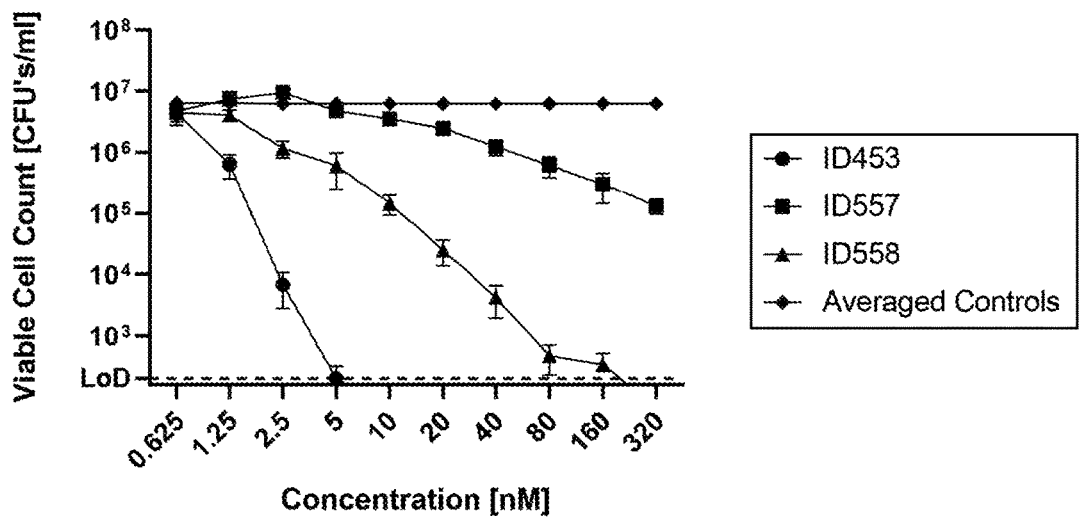

FIG. 4. Killing of *S. epidermidis* ATCC 12228/DSM1798 (MSSE) in human serum by peptidoglycan hydrolases.

Quantitative killing assays (QKAs) were performed for peptidoglycan hydrolase (PGH) constructs ID453, ID557, ID558 in human serum against methicillin-sensitive *Staphylococcus epidermidis* (MSSE) ATCC 12228/DSM1798 at 37° C. for 30 min at 180 rpm (25 mm orbit). Viable cell counts (CFUs/ml) (y-axis) of *S. epidermidis* ATCC 12228/DSM1798 are shown for three PGH constructs in a 2-fold concentration range (x-axis) in nM (320 nM-0.625 nM). The depicted negative control (no addition of PGH) corresponds to the averaged individual controls of the three tested constructs. The limit of detection (LoD) is 200 CFUs/ml (grey dashed line). The y-axis is cut at 160 CFU's/ml. Three biological replicates (n=3) were made, except for concentrations 0.625 and 1.25 nM (n=2). Error bars of averaged controls and constructs represent the standard error of the mean (S.E.M).

Figure 5:
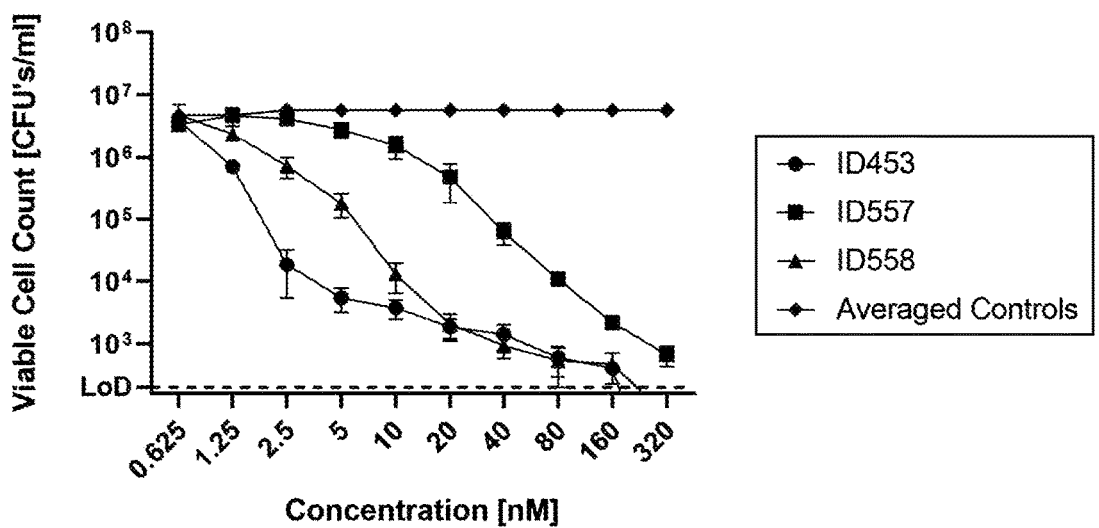

FIG. 5. Killing of *S. epidermidis* ATCC 35984/BB1336 (MRSE) in human serum by peptidoglycan hydrolases.

Quantitative killing assays (QKAs) were performed for peptidoglycan hydrolase (PGH) constructs ID453, ID557, ID558 in human serum against methicillin-resistant (MRSE) ATCC 35984/BB1336 at 37° C. for 30 min at 180 rpm (25 mm orbit). Viable cell counts (CFUs/ml) (y-axis) of *S. epidermidis* ATCC 35984/BB1336 are shown for three PGH constructs in a 2-fold concentration range (x-axis) in nM (320 nM-0.625 nM). The depicted negative control (no addition of PGH) corresponds to the averaged individual controls of the three tested constructs. The limit of detection (LoD) is 200 CFUs/ml (grey dashed line). The y-axis is cut at 160 CFU's/ml. Three biological replicates (n=3) were made, except for concentrations 0.625 and 1.25 nM (n=2). Error bars of averaged controls and constructs represent the standard error of the mean (S.E.M).

EXAMPLES

1. Introduction

Phage lysins are phage-encoded cell wall hydrolases that cleave bonds within the bacterial peptidoglycan, leading to localized dissolution and eventually cell death.

In short, these peptidoglycan hydrolases (PGHs) are modular with one domain being responsible for specific binding to target cell walls and other parts being responsible for cleaving very specific bonds within the peptidoglycan. The modules may be connected by polypeptide linkers. These enzymes display various degrees of specificity for binding to the target and for cleaving certain bonds that may be absent in other bacterial genera or species. By combining and rearranging different parts form various naturally occurring enzymes, novel molecules with very specific recognition and cleavage patterns may be created allowing highly targeted antimicrobial preparations to be made.

Here we present the efficacy profiles in human serum of three such molecules (Table 1). Two of those molecules were already published in WO2021213898 (ID557 [SEQ ID NO: 41] and ID558 [SEQ ID NO: 5]), whereas ID453 is a novel molecule presented herein. All three molecules include the CHAP domain of phage Twort, followed by the M23LST domain of the lysostaphin gene of *Staphylococcus simulans*. Both ID453 and ID557 contain the SH3b domain of the lysostaphin gene whereas ID558 contains a SH3b domain from phage 2638A. The domain and linker origin references are shown in Table 2.

TABLE 1

Overview of constructs, which were compared in the experiments.

| ID | Construct | SEQ ID |
|---|---|---|
| ID453 | CHAPTw(L)_M23LST_SH3bLST | SEQ ID NO: 1 |
| ID557 | CHAPTw_M23LST_SH3bLST | SEQ ID NO: 2 |
| ID558 | CHAPTw(L)_M23LST_(L)SH3b2638 | SEQ ID NO: 3 |

The IDs are listed with the corresponding construct names and domain architecture. ID557 and ID558 are disclosed in WO2021213898 and are listed with the corresponding sequence IDs herein.

TABLE 2

Domains used for the engineering of the constructs and their origins.

| Domain | Organism/Origin | SEQ ID NO: |
|---|---|---|
| CHAPTw | Bacteriophage Twort, endolysin gene | SEQ ID NO: 4 |
| M23LST | *S. simulans* biovar staphylolyticus, lysostaphin gene | SEQ ID NO: 5 |
| SH3bLST | *S. simulans* biovar staphylolyticus, lysostaphin gene | SEQ ID NO: 6 |
| SH3b2638 | Bacteriophage 2638A, endolysin gene | SEQ ID NO: 7 |
| Tw Linker (SVKKKDTKKKPKPSNR DGINKDK) | Bacteriophage Twort, endolysin gene | SEQ ID NO: 8 |
| LST Linker (KAGGTVTPTPNTG) | *S. simulans* biovar staphylolyticus, lysostaphin gene | SEQ ID NO: 9 |
| Ale1 Linker (SNSTSSSNNNG) | *S. capitis* EPK1, ale-1 gene | SEQ ID NO: 10 |
| 2638A Linker (GKLEVSKAATIKQSDV KQEVKKQEAKQIVKATD) | Bacteriophage 2638A, endolysin gene | SEQ ID NO: 11 |

The different domains are listed with the organisms they originate from.

When targeting SBIs, sufficient activity in human serum of candidate molecules is a prerequisite. In this setting efficacy against three *S. aureus* strains including 1 methicillin resistant strain and against one methicillin resistant and one methicillin sensitive *S. epidermidis* strains was investigated. Interestingly, despite significant similarity of the three molecules, one of the candidate compounds showed clear superiority over the other two molecules. ID453 performed better than the others, requiring a lower dose to achieve complete killing of target cells in human serum for two of the three *S. aureus* strains tested and also for one of the two *S. epidermidis* strains investigated. It was shown to be at least as effective as either of the other compounds on the remaining strains, with a higher killing potency at lower concentrations as compared to the other constructs. For targeting SBIs, ID453 is a superior option.

2. Results 2.1 Quantitative Killing Assays

Quantitative killing assays (QKAs) were performed at 37° C. and 180 rpm (25 mm orbit) for 30 min in human serum with the peptidoglycan hydrolase (PGH) constructs CHAPTw(L)_M23LST_SH3bLST (ID453), CHAPTw_M23LST_SH3bLST (ID557) and CHAPTw(L)_M23LST_(L)SH3b2638 (ID558) against *S. aureus* NR-46543/USA300 JE2, *S. aureus* ATCC 12600, *S. aureus* ATCC 12598 (Cowan I), *S. epidermidis* ATCC 12228/DSM1798 and *S. epidermidis* ATCC 35984/BB1336. The constructs were tested in a 2-fold concentration range (320 nM-0.625 nM). The evaluated results of the QKAs (viable cell counts) of the three constructs in human serum are shown in FIGS. 1-5. Three biological replicates were performed for each construct in each strain. As shown in FIGS.

1-5, all three constructs have staphylolytic activity in each strain within the tested concentration range. Furthermore, a dose-response is apparent. The further to the left a curve is positioned, the more active a construct is.

ID453 is the construct with the highest killing activity against the methicillin resistant *S. aureus* NR-46543/USA300 JE2 (FIG. 1) and the methicillin sensitive *S. aureus* ATCC 12598 (Cowan I) (FIG. 3) strains, followed by ID557. Although the difference in activity is not as pronounced between these two constructs against the methicillin sensitive *S. aureus* ATCC 12600 (FIG. 2) strain, ID453 still showed higher activity than the other constructs at most of the tested concentrations. In all three strains, ID558 showed the lowest activity.

The superiority of ID453 is most apparent against the methicillin sensitive *S. epidermidis* ATCC 12228/DSM1798 (FIG. 4) strain. In contrast to the results obtained with the *S. aureus* strains, ID557 is the construct with the lowest activity when tested against *S. epidermidis* strains. Although ID453 shows similar activity as construct ID558 against the methicillin resistant *S. epidermidis* ATCC 35984/BB1336 strain at higher concentrations (>20 nM), ID453 is clearly superior at lower concentrations (<20 nM) (FIG. 5). Overall, our data demonstrated superiority of ID453 as compared to the other tested constructs.

3. Materials and Methods 3.1 Materials: Bacteria, Media, Buffers, Devices, Consumables

TABLE 3

Bacteria, which were used for the experimentation.

| Bacterial Strain | Article Nr. | Supplier |
|---|---|---|
| *S. aureus* NR-46543/USA300 JE2 (MRSA) | NR-46543 | NARSA, ETH |
| *S. aureus* ATCC 12600/DSM20231 (MSSA) | DSM20231 | DSMZ |
| *S. aureus* ATCC 12598/DSM20372 (MSSA) (Cowan I) | DSM20372 | DSMZ |
| *S. epidermidis* ATCC 12228/DSM1798 (MSSE) | DSM1798 | DSMZ |
| *S. epidermidis* ATCC 35984/BB1336 (MRSE) | ATCC 35984 | Berger-Bächi, UZH |

The bacterial strains are listed with the corresponding article number, and supplier.

TABLE 4

List of media and buffers used for the experimentation.

| Media/Buffer | Component | Amount/L | PH | Protocol |
|---|---|---|---|---|
| Tryptic Soy Broth (TSB) medium | Caso Bouillon (ready mixed) | 30 g | 7.3 | Dissolve 30 g/L of the ready mixed powder in dH2O, adjust pH using 10M NaOH. Autoclave. |
| Tryptic Soy Broth (TSB) agar plates | Caso Bouillon (ready mixed) Agar | 30 g 15 g | 7.3 | Dissolve the reagents in dH$_2$O, adjust pH using 10M NaOH. Autoclave. |
| LB agar, ready mixed (Square agar plates) | Tryptone Yest Extract NaCl (171 mM) Agar | 10 g 5 g 10 g 15 g | 7.4 | Dissolve 40 g/L of the ready mixed powder in dH$_2$O, adjust pH using 10M NaOH. Autoclave. Cool to 55° C. and pour 70 ml per square plate. |
| 10x Stopping buffer [To produce ca. 40 ml] | Trisodium citrate (dihydrate) Citric acid (monohydrate) | 113.75 g [4.35 g] 136 g [5.44 g] | — | Weigh both components in separate bottles/50 ml Falcon tubes. Add 905 g [36.2 g] upH$_2$O to the trisodium citrate bottle/tube and dissolve by swirling or vortexing. When the solution is completely dissolved, pour the solution to the citric acid bottle/tube and dissolve by swirling or vortexing. Sterile filter with 0.22 μm PES-membrane filter. Store at 4° C., light protected, and the shelf life is 1 month. |
| 1x Stopping buffer | | | | Prepare 1x stopping buffer by making a 1:10 dilution of 10x stopping buffer with upH$_2$O. Sterile filter with 0.22 μm PES-membrane filter. Store at 4° C., light protected, and the shelf life is 1 month. |

For each medium and buffer the components with the corresponding amount per litre, the pH and the protocol are listed.

TABLE 5

Chemicals, which were used for experimentation.

| Material | Article Nr. | Supplier | Lot Nr. |
|---|---|---|---|
| Caso Bouillon (ready mixed) | 413820.1210 | HuberLab | C203081 |
| LB-Agar (ready mixed) | A0927.1000KG | HuberLab | 0927-1/103, |
| Agar-Agar | 5210.4 | Carl Roth | 489289238 |
| Trisodium citrate (dihydrate) | S1804-500G | Sigma-Aldrich (Merck) | BCBX4142 |
| Citric acid (monohydrate) | C1909-500G | Sigma-Aldrich (Merck) | SLCF3211 |
| Human Serum, normal | S1-LITER | Sigma-Aldrich (Merck) | 3717696 |

The chemicals are listed with the corresponding article number, supplier and lot number.

TABLE 6

List of devices and consumables, which were used for the experimentation.

| Name | Model/Article Nr. | Brand/Supplier |
|---|---|---|
| Climo Shaker [Incubator Shaker] | ISF1-X | Kühner |
| Incucenter [Incubator] | IC80 | SalvisLab |
| Water bath | 1113 | GFL |

TABLE 6-continued

List of devices and consumables, which were used for the experimentation.

| Name | Model/Article Nr. | Brand/Supplier |
|---|---|---|
| Spectrophotometer | Nanodrop One$^c$ | Thermo Fisher Scientific |
| Vortex | Vortex Genie 2 | Scientific Industries |
| Mini-Vortex | Mini Vortex Mixer | Fisher Scientific |
| Vacuum pump | BVC Professional | Vacuubrand |
| Mini-Centrifuge | Z 130 M | Hermle |
| EVOLVE Pipette 1-Channel, 1-10 µl | 3012 | Integra |
| EVOLVE Pipette 1-Channel, 20-200 µl | 3016 | Integra |
| EVOLVE Pipette 1-Channel, 100-1000 µl | 3018 | Integra |
| EVOLVE Pipette 12-Channel, 1-10 µl | 3032 | Integra |
| EVOLVE Pipette 12-Channel, 10-100 µl | 3035 | Integra |
| VOYAGER Pipette 8-Channel, 50-1250 µl | 4724 | Integra |
| VOYAGER Pipette 12-Channel, 5-125 µl | 4732 | Integra |
| Semi-micro cuvettes (Greiner Bio-One) | 7.613 101 | HuberLab |
| 1.5 ml Eppendorf Tubes, Safe-lock | 11.3817.01 | HuberLab |
| 96-well Plate [F-Bottom, sterile, with lid] | 400096 | Bioswisstec |
| 25 ml SureFlo Reservoir | 4382 | Integra |
| 100 ml SureFlo Reservoir | 4392 | Integra |
| Inoculation loops | 7.731 170 | HuberLab |
| Filtropur S PES Filter, 0.45 µm | 83.1826 | Sarstedt |
| 20 ml Syringe (Codan) | 3.7410.08 | HuberLab |
| 50 ml/60 ml Syringe (Codan) | 3.7414.12 | HuberLab |
| Serological Pipettes 10 ml (Greiner Bio-One) | 7.607 180 | HuberLab |
| Serological Pipettes 50 ml (Greiner Bio-One) | 7.768 180 | HuberLab |
| 500 ml Bottle-Top 0.22 µm PES Filter (Nalgene) | 29669 | Milian |
| 50 ml Falcon Tube | 50050 | Bioswisstec |

Each device/consumable is listed with its corresponding model, brand, and serial/article number.

3.2 Methods: Protocol and Procedure 3.2.1 Quantitative Killing Assay (QKA)

In total, three PGH constructs were tested in human serum against three *S. aureus* and two *S. epidermidis* strains. The aliquots of the constructs were stored in PCR tubes at −80° C. (in CIEX PO4 Elution buffer). If not mentioned otherwise, all steps were performed under sterile conditions. A final PGH concentration range of 320 nM, 160 nM, 80 nM, 40 nM, 20 nM, 10 nM, 5 nM, 2.5 nM, 1.25 nM and 0.625 nM was tested against all five strains. The desired final bacterial control was between $1 \times 10^6$-$1 \times 10^7$ CFUs/ml. At least two biological replicates were performed. One 96-well F-bottom plate was used for each PGH construct to be tested.

Precultures were prepared by inoculating 5 ml tryptic soy broth (TSB) medium with either *S. aureus* NR-46543/USA300 JE2, *S. aureus* ATCC 12600, *S. aureus* ATCC 12598 (Cowan I), *S. epidermidis* ATCC 12228/DSM1798 or *S. epidermidis* ATCC 35984/BB1336. Cultures were incubated at 37° C. and 180 revolutions per minute (rpm) (25 mm orbit) overnight (O/N).

An aliquot of human serum (stored at −20° C.) was thawed in the water bath at 30° C., filtered using a 0.45 µm filter and was stored on ice. A 1:25 dilution of the O/N culture was made by mixing 400 µl O/N culture with 10 ml TSB medium, and the culture was incubated at 37° C. and 180 rpm until an optical density (OD600 nm) of 0.5-0.6 was reached. The culture was then put on ice for ~5 min to stop growth. 1 ml of the culture was adjusted to an OD of 0.51 with TSB medium, transferred to a 1.5 ml reaction tube and placed on ice. While the culture was growing, 160 µl 1× stopping buffer was provided in each 96-well F-Bottom plate in rows B-H, and plates were stored at 4° C. until use. Once bacterial cultures had been adjusted to the desired OD, suitable aliquots (10-20 µl aliquots) of the PGH constructs to be tested were thawed on ice and briefly spun down. The human serum was acclimatized to RT. 100 µl of human serum were provided via reverse pipetting into the wells A1 and A3-A12 of the prepared 96-well F-Bottom plates (one plate per enzyme to be tested). In well A2 of each plate, the enzyme predilution of the respective construct to be tested in human serum (final volume 200 µl) was prepared to reach a concentration twice as high (640 nM) as the highest final concentration (320 nM) to be tested. The enzyme predilution was mixed well, and a 2-fold dilution series was made by transferring 100 µl from well A2 to well A3, mixing six times and changing pipette tips, continuing with the same procedure from well A3 to A4 and so on until well A11. The last 100 µl were discarded from well A11 leaving wells A1 and A12 as negative controls (no addition of enzyme, only addition of bacterial suspension in serum). Each enzyme predilution and dilution series in the plates was prepared no more than 10 min prior to inoculation to minimize interaction of the enzymes with the walls of the plate wells. The bacterial suspension for inoculation was prepared by mixing 500 µl of the vortexed, OD-adjusted culture with 4.5 ml of human serum (1:10 dilution) in a 25 ml reservoir. Using a manual multichannel pipette, 100 µl of bacterial suspension from the reservoir were added to wells A1-A12 of the plate, mixed one time by pipetting up and down and the plate was immediately transferred to the Incubator Shaker at 37° C. and 180 rpm for exactly 30 min.

After the incubation of the plate for exactly 30 min, the plate was removed from the Incubator Shaker, and 20 µl 10× stopping buffer were immediately added to row A with a multichannel pipette. The suspensions in the wells were homogenized by pipetting up and down eight times to stop further activity of the enzyme. Then, a 5-fold dilution series was made in the provided 1× stopping buffer by transferring 40 µl from row A to row B, mixing six times, changing pipette tips and then transferring 40 µl from row B to C and so on until row H. The last 40 µl were discarded from row H. From each well of the 96-well plate, 5.5 µl were spot-plated on a pre-dried LB agar square plate. After the spots were dried, the agar plates were placed in an incubator upside down at 37° C. for O/N incubation (*S. aureus* strains for ~16 h and *S. epidermidis* strains for ~20 h).

The following day, colony forming units (CFUs) per spot were counted. CFUs/ml were calculated, and viable cell count and CFUs/ml log reduction across the tested final concentration range (320 nM-0.625 nM) were visualized in graphs (GraphPad Prism 9.2.0). Results of biological replicates were averaged and the standard error of the mean (S.E.M) was calculated and displayed.

REFERENCES

Antimicrobial Resistance Collaborators. Global burden of bacterial antimicrobial resistance in 2019: a systematic analysis. Lancet. 2022 Feb. 12; 399(10325):629-655. doi: 10.1016/S0140-6736(21)02724-0. Epub 2022 Jan. 19. PMID: 35065702; PMCID: PMC8841637.

Kleinschmidt S, Huygens F, Faoagali J, Rathnayake I U, Hafner L M. *Staphylococcus epidermidis* as a cause of bacteremia. Future Microbiol. 2015; 10(11):1859-79. doi: 10.2217/fmb.15.98. Epub 2015 Oct. 30. PMID: 26517189.

Guo Y, Song G, Sun M, Wang J, Wang Y. Prevalence and Therapies of Antibiotic-Resistance in *Staphylococcus aureus*. Front Cell Infect Microbiol. 2020 Mar. 17; 10:107. doi: 10.3389/fcimb.2020.00107. PMID: 32257966; PMCID: PMC7089872.

Grundling, A., Missiakas, D. M. & Schneewind, O., 2006. *Staphylococcus aureus* Mutants with Increased Lysostaphin Resistance. *Journal of Bacteriology*, 188(17), pp. 6286-6297.

Kashani, H. et al., 2017. Recombinant Endolysins as Potential Therapeutics against Antibiotic-Resistant *Staphylococcus aureus*: Current Status of Research and Novel Delivery Strategies. *Clinical Microbiology Reviews*, 31(1).

Korndörfer, I. P. et al., 2006. The Crystal Structure of the Bacteriophage PSA Endolysin Reveals a Unique Fold Responsible for Specific Recognition of *Listeria* Cell Walls. *Journal of Molecular Biology*, 364(4), pp. 678-689.

Schmelcher, M. et al., 2015. Evolutionarily distinct bacteriophage endolysins featuring conserved peptidoglycan cleavage sites protect mice from MRSA infection. *Journal of Antimicrobial Chemotherapy*, 70(5), pp. 1453-1465.

Schmelcher, M., Donovan, D. M. & Loessner, M. J., 2012. Bacteriophage endolysins as novel antimicrobials. *Future Microbiology*, 7(10), pp. 1147-1171.

```
                          SEQUENCE LISTING

Sequence total quantity: 161
SEQ ID NO: 1             moltype = AA   length = 417
FEATURE                  Location/Qualifiers
source                   1..417
                         mol_type = protein
                         organism = synthetic construct
SEQUENCE: 1
MKTLKQAESY IKSKVNTGTD FDGLYGYQCM DLAVDYIYHV TDGKIRMWGN AKDAINNSFG    60
GTATVYKNYP AFRPKYGDVV VWTTGNFATY GHIAIVTNPD PYGDLQYVTV LEQNWNGNGI   120
YKTELATIRT HDYTGITHFI RPNFATESSV KKKDTKKKPK PSNRDGINKD KAATHEHSAQ   180
WLNNYKKGYG YGPYPLGING GMHYGVDFFM NIGTPVKAIS SGKIVEAGWS NYGGGNQIGL   240
IENDGVHRQW YMHLSKYNVK VGDYVKAGQI IGWSGSTGYS TAPHLHFQRM VNSFSNSTAQ   300
DPMPFLKSAG YGKAGGTVTP TPNTGWKTNK YGTLYKSESA SFTPNTDIIT RTTGPFRSMP   360
QSGVLKAGQT IHYDEVMKQD GHVWVGYTGN SGQRIYLPVR TWNKSTNTLG VLWGTIK      417

SEQ ID NO: 2             moltype = AA   length = 403
FEATURE                  Location/Qualifiers
source                   1..403
                         mol_type = protein
                         organism = synthetic construct
SEQUENCE: 2
MKTLKQAESY IKSKVNTGTD FDGLYGYQCM DLAVDYIYHV TDGKIRMWGN AKDAINNSFG    60
GTATVYKNYP AFRPKYGDVV VWTTGNFATY GHIAIVTNPD PYGDLQYVTV LEQNWNGNGI   120
YKTELATIRT HDYTGITHFI RPNFATESSN STSSSNNNGA ATHEHSAQWL NNYKKGYGYG   180
PYPLGINGGM HYGVDFFMNI GTPVKAISSG KIVEAGWSNY GGGNQIGLIE NDGVHRQWYM   240
HLSKYNVKVG DYVKAGQIIG WSGSTGYSTA PHLHFQRMVN SFSNSTAQDP MPFLKSAGYG   300
SNSTSSSNNN GWKTNKYGTL YKSESASFTP NTDIITRTTG PFRSMPQSGV LKAGQTIHYD   360
EVMKQDGHVW VGYTGNSGQR IYLPVRTWNK STNTLGVLWG TIK                     403

SEQ ID NO: 3             moltype = AA   length = 439
FEATURE                  Location/Qualifiers
source                   1..439
                         mol_type = protein
                         organism = synthetic construct
SEQUENCE: 3
MKTLKQAESY IKSKVNTGTD FDGLYGYQCM DLAVDYIYHV TDGKIRMWGN AKDAINNSFG    60
GTATVYKNYP AFRPKYGDVV VWTTGNFATY GHIAIVTNPD PYGDLQYVTV LEQNWNGNGI   120
YKTELATIRT HDYTGITHFI RPNFATESSV KKKDTKKKPK PSNRDGINKD KAATHEHSAQ   180
WLNNYKKGYG YGPYPLGING GMHYGVDFFM NIGTPVKAIS SGKIVEAGWS NYGGGNQIGL   240
IENDGVHRQW YMHLSKYNVK VGDYVKAGQI IGWSGSTGYS TAPHLHFQRM VNSFSNSTAQ   300
DPMPFLKSAG YGGKLEVSKA ATIKQSDVKQ EVKKQEAKQI VKATDWKQNK DGIWYKAEHA   360
SFTVTAPEGI ITRYKGPWTG HPQAGVLQKG QTIKYDEVQK FDGHVWVSWE TFEGETVYMP   420
VRTWDAKTGK VGKLWGEIK                                                439

SEQ ID NO: 4             moltype = AA   length = 148
FEATURE                  Location/Qualifiers
source                   1..148
                         mol_type = protein
                         organism = synthetic construct
SEQUENCE: 4
MKTLKQAESY IKSKVNTGTD FDGLYGYQCM DLAVDYIYHV TDGKIRMWGN AKDAINNSFG    60
GTATVYKNYP AFRPKYGDVV VWTTGNFATY GHIAIVTNPD PYGDLQYVTV LEQNWNGNGI   120
YKTELATIRT HDYTGITHFI RPNFATES                                      148

SEQ ID NO: 5             moltype = AA   length = 141
FEATURE                  Location/Qualifiers
source                   1..141
                         mol_type = protein
```

```
                                    organism = synthetic construct
SEQUENCE: 5
AATHEHSAQW LNNYKKGYGY GPYPLGINGG MHYGVDFFMN IGTPVKAISS GKIVEAGWSN    60
YGGGNQIGLI ENDGVHRQWY MHLSKYNVKV GDYVKAGQII GWSGSTGYST APHLHFQRMV   120
NSFSNSTAQD PMPFLKSAGY G                                             141

SEQ ID NO: 6            moltype = AA   length = 92
FEATURE                 Location/Qualifiers
source                  1..92
                        mol_type = protein
                        organism = synthetic construct
SEQUENCE: 6
WKTNKYGTLY KSESASFTPN TDIITRTTGP FRSMPQSGVL KAGQTIHYDE VMKQDGHVWV    60
GYTGNSGQRI YLPVRTWNKS TNTLGVLWGT IK                                  92

SEQ ID NO: 7            moltype = AA   length = 94
FEATURE                 Location/Qualifiers
source                  1..94
                        mol_type = protein
                        organism = synthetic construct
SEQUENCE: 7
WKQNKDGIWY KAEHASFTVT APEGIITRYK GPWTGHPQAG VLQKGQTIKY DEVQKFDGHV    60
WVSWETFEGE TVYMPVRTWD AKTGKVGKLW GEIK                                94

SEQ ID NO: 8            moltype = AA   length = 23
FEATURE                 Location/Qualifiers
source                  1..23
                        mol_type = protein
                        organism = synthetic construct
SEQUENCE: 8
SVKKKDTKKK PKPSNRDGIN KDK                                            23

SEQ ID NO: 9            moltype = AA   length = 13
FEATURE                 Location/Qualifiers
source                  1..13
                        mol_type = protein
                        organism = synthetic construct
SEQUENCE: 9
KAGGTVTPTP NTG                                                       13

SEQ ID NO: 10           moltype = AA   length = 11
FEATURE                 Location/Qualifiers
source                  1..11
                        mol_type = protein
                        organism = synthetic construct
SEQUENCE: 10
SNSTSSSNNN G                                                         11

SEQ ID NO: 11           moltype = AA   length = 33
FEATURE                 Location/Qualifiers
source                  1..33
                        mol_type = protein
                        organism = synthetic construct
SEQUENCE: 11
GKLEVSKAAT IKQSDVKQEV KKQEAKQIVK ATD                                 33

SEQ ID NO: 12           moltype = AA   length = 23
FEATURE                 Location/Qualifiers
source                  1..23
                        mol_type = protein
                        organism = synthetic construct
SEQUENCE: 12
SVKKKDTKKK PKPSNRDGIN KDK                                            23

SEQ ID NO: 13           moltype = AA   length = 22
FEATURE                 Location/Qualifiers
source                  1..22
                        mol_type = protein
                        organism = synthetic construct
SEQUENCE: 13
VKKKDTKKKP KPSNRDGINK DK                                             22

SEQ ID NO: 14           moltype = AA   length = 21
FEATURE                 Location/Qualifiers
source                  1..21
                        mol_type = protein
                        organism = synthetic construct
SEQUENCE: 14
KKKDTKKKPK PSNRDGINKD K                                              21
```

```
SEQ ID NO: 15              moltype = AA  length = 20
FEATURE                    Location/Qualifiers
source                     1..20
                           mol_type = protein
                           organism = unidentified
SEQUENCE: 15
KKDTKKKPKP SNRDGINKDK                                                        20

SEQ ID NO: 16              moltype = AA  length = 19
FEATURE                    Location/Qualifiers
source                     1..19
                           mol_type = protein
                           organism = synthetic construct
SEQUENCE: 16
KDTKKKPKPS NRDGINKDK                                                         19

SEQ ID NO: 17              moltype = AA  length = 18
FEATURE                    Location/Qualifiers
source                     1..18
                           mol_type = protein
                           organism = synthetic construct
SEQUENCE: 17
DTKKKPKPSN RDGINKDK                                                          18

SEQ ID NO: 18              moltype = AA  length = 17
FEATURE                    Location/Qualifiers
source                     1..17
                           mol_type = protein
                           organism = synthetic construct
SEQUENCE: 18
TKKKPKPSNR DGINKDK                                                           17

SEQ ID NO: 19              moltype = AA  length = 16
FEATURE                    Location/Qualifiers
source                     1..16
                           mol_type = protein
                           organism = synthetic construct
SEQUENCE: 19
KKKPKPSNRD GINKDK                                                            16

SEQ ID NO: 20              moltype = AA  length = 15
FEATURE                    Location/Qualifiers
source                     1..15
                           mol_type = protein
                           organism = synthetic construct
SEQUENCE: 20
KKPKPSNRDG INKDK                                                             15

SEQ ID NO: 21              moltype = AA  length = 14
FEATURE                    Location/Qualifiers
source                     1..14
                           mol_type = protein
                           organism = unidentified
SEQUENCE: 21
KPKPSNRDGI NKDK                                                              14

SEQ ID NO: 22              moltype = AA  length = 13
FEATURE                    Location/Qualifiers
source                     1..13
                           mol_type = protein
                           organism = synthetic construct
SEQUENCE: 22
PKPSNRDGIN KDK                                                               13

SEQ ID NO: 23              moltype = AA  length = 12
FEATURE                    Location/Qualifiers
source                     1..12
                           mol_type = protein
                           organism = synthetic construct
SEQUENCE: 23
KPSNRDGINK DK                                                                12

SEQ ID NO: 24              moltype = AA  length = 11
FEATURE                    Location/Qualifiers
source                     1..11
                           mol_type = protein
                           organism = synthetic construct
SEQUENCE: 24
```

-continued

```
PSNRDGINKD K                                                                11

SEQ ID NO: 25           moltype = AA  length = 10
FEATURE                 Location/Qualifiers
source                  1..10
                        mol_type = protein
                        organism = synthetic construct
SEQUENCE: 25
SNRDGINKDK                                                                  10

SEQ ID NO: 26           moltype = AA  length = 22
FEATURE                 Location/Qualifiers
source                  1..22
                        mol_type = protein
                        organism = synthetic construct
SEQUENCE: 26
SVKKKDTKKK PKPSNRDGIN KD                                                    22

SEQ ID NO: 27           moltype = AA  length = 21
FEATURE                 Location/Qualifiers
source                  1..21
                        mol_type = protein
                        organism = synthetic construct
SEQUENCE: 27
VKKKDTKKKP KPSNRDGINK D                                                     21

SEQ ID NO: 28           moltype = AA  length = 20
FEATURE                 Location/Qualifiers
source                  1..20
                        mol_type = protein
                        organism = synthetic construct
SEQUENCE: 28
KKKDTKKKPK PSNRDGINKD                                                       20

SEQ ID NO: 29           moltype = AA  length = 19
FEATURE                 Location/Qualifiers
source                  1..19
                        mol_type = protein
                        organism = synthetic construct
SEQUENCE: 29
KKDTKKKPKP SNRDGINKD                                                        19

SEQ ID NO: 30           moltype = AA  length = 18
FEATURE                 Location/Qualifiers
source                  1..18
                        mol_type = protein
                        organism = synthetic construct
SEQUENCE: 30
KDTKKKPKPS NRDGINKD                                                         18

SEQ ID NO: 31           moltype = AA  length = 17
FEATURE                 Location/Qualifiers
source                  1..17
                        mol_type = protein
                        organism = synthetic construct
SEQUENCE: 31
DTKKKPKPSN RDGINKD                                                          17

SEQ ID NO: 32           moltype = AA  length = 16
FEATURE                 Location/Qualifiers
source                  1..16
                        mol_type = protein
                        organism = synthetic construct
SEQUENCE: 32
TKKKPKPSNR DGINKD                                                           16

SEQ ID NO: 33           moltype = AA  length = 15
FEATURE                 Location/Qualifiers
source                  1..15
                        mol_type = protein
                        organism = synthetic construct
SEQUENCE: 33
KKKPKPSNRD GINKD                                                            15

SEQ ID NO: 34           moltype = AA  length = 14
FEATURE                 Location/Qualifiers
source                  1..14
                        mol_type = protein
                        organism = synthetic construct
```

```
SEQUENCE: 34
KKPKPSNRDG INKD                                                        14

SEQ ID NO: 35          moltype = AA  length = 13
FEATURE                Location/Qualifiers
source                 1..13
                       mol_type = protein
                       organism = synthetic construct
SEQUENCE: 35
KPKPSNRDGI NKD                                                         13

SEQ ID NO: 36          moltype = AA  length = 12
FEATURE                Location/Qualifiers
source                 1..12
                       mol_type = protein
                       organism = synthetic construct
SEQUENCE: 36
PKPSNRDGIN KD                                                          12

SEQ ID NO: 37          moltype = AA  length = 11
FEATURE                Location/Qualifiers
source                 1..11
                       mol_type = protein
                       organism = synthetic construct
SEQUENCE: 37
KPSNRDGINK D                                                           11

SEQ ID NO: 38          moltype = AA  length = 10
FEATURE                Location/Qualifiers
source                 1..10
                       mol_type = protein
                       organism = synthetic construct
SEQUENCE: 38
PSNRDGINKD                                                             10

SEQ ID NO: 39          moltype = AA  length = 21
FEATURE                Location/Qualifiers
source                 1..21
                       mol_type = protein
                       organism = synthetic construct
SEQUENCE: 39
SVKKKDTKKK PKPSNRDGIN K                                                21

SEQ ID NO: 40          moltype = AA  length = 20
FEATURE                Location/Qualifiers
source                 1..20
                       mol_type = protein
                       organism = synthetic construct
SEQUENCE: 40
VKKKDTKKKP KPSNRDGINK                                                  20

SEQ ID NO: 41          moltype = AA  length = 19
FEATURE                Location/Qualifiers
source                 1..19
                       mol_type = protein
                       organism = synthetic construct
SEQUENCE: 41
KKKDTKKKPK PSNRDGINK                                                   19

SEQ ID NO: 42          moltype = AA  length = 18
FEATURE                Location/Qualifiers
source                 1..18
                       mol_type = protein
                       organism = synthetic construct
SEQUENCE: 42
KKDTKKKPKP SNRDGINK                                                    18

SEQ ID NO: 43          moltype = AA  length = 17
FEATURE                Location/Qualifiers
source                 1..17
                       mol_type = protein
                       organism = synthetic construct
SEQUENCE: 43
KDTKKKPKPS NRDGINK                                                     17

SEQ ID NO: 44          moltype = AA  length = 16
FEATURE                Location/Qualifiers
source                 1..16
                       mol_type = protein
```

```
                              -continued
                           organism = synthetic construct
SEQUENCE: 44
DTKKKPKPSN RDGINK                                                    16

SEQ ID NO: 45              moltype = AA  length = 15
FEATURE                    Location/Qualifiers
source                     1..15
                           mol_type = protein
                           organism = synthetic construct
SEQUENCE: 45
TKKKPKPSNR DGINK                                                     15

SEQ ID NO: 46              moltype = AA  length = 14
FEATURE                    Location/Qualifiers
source                     1..14
                           mol_type = protein
                           organism = synthetic construct
SEQUENCE: 46
KKKPKPSNRD GINK                                                      14

SEQ ID NO: 47              moltype = AA  length = 13
FEATURE                    Location/Qualifiers
source                     1..13
                           mol_type = protein
                           organism = synthetic construct
SEQUENCE: 47
KKPKPSNRDG INK                                                       13

SEQ ID NO: 48              moltype = AA  length = 12
FEATURE                    Location/Qualifiers
source                     1..12
                           mol_type = protein
                           organism = synthetic construct
SEQUENCE: 48
KPKPSNRDGI NK                                                        12

SEQ ID NO: 49              moltype = AA  length = 11
FEATURE                    Location/Qualifiers
source                     1..11
                           mol_type = protein
                           organism = synthetic construct
SEQUENCE: 49
PKPSNRDGIN K                                                         11

SEQ ID NO: 50              moltype = AA  length = 10
FEATURE                    Location/Qualifiers
source                     1..10
                           mol_type = protein
                           organism = unidentified
SEQUENCE: 50
KPSNRDGINK                                                           10

SEQ ID NO: 51              moltype = AA  length = 20
FEATURE                    Location/Qualifiers
source                     1..20
                           mol_type = protein
                           organism = synthetic construct
SEQUENCE: 51
SVKKKDTKKK PKPSNRDGIN                                                20

SEQ ID NO: 52              moltype = AA  length = 19
FEATURE                    Location/Qualifiers
source                     1..19
                           mol_type = protein
                           organism = synthetic construct
SEQUENCE: 52
VKKKDTKKKP KPSNRDGIN                                                 19

SEQ ID NO: 53              moltype = AA  length = 18
FEATURE                    Location/Qualifiers
source                     1..18
                           mol_type = protein
                           organism = synthetic construct
SEQUENCE: 53
KKKDTKKKPK PSNRDGIN                                                  18

SEQ ID NO: 54              moltype = AA  length = 17
FEATURE                    Location/Qualifiers
source                     1..17
```

```
                              mol_type = protein
                              organism = synthetic construct
SEQUENCE: 54
KKDTKKKPKP SNRDGIN                                                    17

SEQ ID NO: 55                 moltype = AA   length = 16
FEATURE                       Location/Qualifiers
source                        1..16
                              mol_type = protein
                              organism = synthetic construct
SEQUENCE: 55
KDTKKKPKPS NRDGIN                                                     16

SEQ ID NO: 56                 moltype = AA   length = 15
FEATURE                       Location/Qualifiers
source                        1..15
                              mol_type = protein
                              organism = synthetic construct
SEQUENCE: 56
DTKKKPKPSN RDGIN                                                      15

SEQ ID NO: 57                 moltype = AA   length = 14
FEATURE                       Location/Qualifiers
source                        1..14
                              mol_type = protein
                              organism = synthetic construct
SEQUENCE: 57
TKKKPKPSNR DGIN                                                       14

SEQ ID NO: 58                 moltype = AA   length = 13
FEATURE                       Location/Qualifiers
source                        1..13
                              mol_type = protein
                              organism = synthetic construct
SEQUENCE: 58
KKKPKPSNRD GIN                                                        13

SEQ ID NO: 59                 moltype = AA   length = 12
FEATURE                       Location/Qualifiers
source                        1..12
                              mol_type = protein
                              organism = synthetic construct
SEQUENCE: 59
KKPKPSNRDG IN                                                         12

SEQ ID NO: 60                 moltype = AA   length = 11
FEATURE                       Location/Qualifiers
source                        1..11
                              mol_type = protein
                              organism = synthetic construct
SEQUENCE: 60
KPKPSNRDGI N                                                          11

SEQ ID NO: 61                 moltype = AA   length = 10
FEATURE                       Location/Qualifiers
source                        1..10
                              mol_type = protein
                              organism = synthetic construct
SEQUENCE: 61
PKPSNRDGIN                                                            10

SEQ ID NO: 62                 moltype = AA   length = 19
FEATURE                       Location/Qualifiers
source                        1..19
                              mol_type = protein
                              organism = synthetic construct
SEQUENCE: 62
SVKKKDTKKK PKPSNRDGI                                                  19

SEQ ID NO: 63                 moltype = AA   length = 18
FEATURE                       Location/Qualifiers
source                        1..18
                              mol_type = protein
                              organism = synthetic construct
SEQUENCE: 63
VKKKDTKKKP KPSNRDGI                                                   18

SEQ ID NO: 64                 moltype = AA   length = 17
FEATURE                       Location/Qualifiers
```

```
source                      1..17
                            mol_type = protein
                            organism = synthetic construct
SEQUENCE: 64
KKKDTKKKPK PSNRDGI                                                         17

SEQ ID NO: 65               moltype = AA  length = 16
FEATURE                     Location/Qualifiers
source                      1..16
                            mol_type = protein
                            organism = synthetic construct
SEQUENCE: 65
KKDTKKKPKP SNRDGI                                                          16

SEQ ID NO: 66               moltype = AA  length = 15
FEATURE                     Location/Qualifiers
source                      1..15
                            mol_type = protein
                            organism = synthetic construct
SEQUENCE: 66
KDTKKKPKPS NRDGI                                                           15

SEQ ID NO: 67               moltype = AA  length = 14
FEATURE                     Location/Qualifiers
source                      1..14
                            mol_type = protein
                            organism = synthetic construct
SEQUENCE: 67
DTKKKPKPSN RDGI                                                            14

SEQ ID NO: 68               moltype = AA  length = 13
FEATURE                     Location/Qualifiers
source                      1..13
                            mol_type = protein
                            organism = synthetic construct
SEQUENCE: 68
TKKKPKPSNR DGI                                                             13

SEQ ID NO: 69               moltype = AA  length = 12
FEATURE                     Location/Qualifiers
source                      1..12
                            mol_type = protein
                            organism = synthetic construct
SEQUENCE: 69
KKKPKPSNRD GI                                                              12

SEQ ID NO: 70               moltype = AA  length = 11
FEATURE                     Location/Qualifiers
source                      1..11
                            mol_type = protein
                            organism = synthetic construct
SEQUENCE: 70
KKPKPSNRDG I                                                               11

SEQ ID NO: 71               moltype = AA  length = 10
FEATURE                     Location/Qualifiers
source                      1..10
                            mol_type = protein
                            organism = synthetic construct
SEQUENCE: 71
KPKPSNRDGI                                                                 10

SEQ ID NO: 72               moltype = AA  length = 18
FEATURE                     Location/Qualifiers
source                      1..18
                            mol_type = protein
                            organism = synthetic construct
SEQUENCE: 72
SVKKKDTKKK PKPSNRDG                                                        18

SEQ ID NO: 73               moltype = AA  length = 17
FEATURE                     Location/Qualifiers
source                      1..17
                            mol_type = protein
                            organism = synthetic construct
SEQUENCE: 73
VKKKDTKKKP KPSNRDG                                                         17

SEQ ID NO: 74               moltype = AA  length = 16
```

```
FEATURE                 Location/Qualifiers
source                  1..16
                        mol_type = protein
                        organism = synthetic construct
SEQUENCE: 74
KKKDTKKKPK PSNRDG                                                           16

SEQ ID NO: 75           moltype = AA  length = 15
FEATURE                 Location/Qualifiers
source                  1..15
                        mol_type = protein
                        organism = synthetic construct
SEQUENCE: 75
KKDTKKKPKP SNRDG                                                            15

SEQ ID NO: 76           moltype = AA  length = 14
FEATURE                 Location/Qualifiers
source                  1..14
                        mol_type = protein
                        organism = synthetic construct
SEQUENCE: 76
KDTKKKPKPS NRDG                                                             14

SEQ ID NO: 77           moltype = AA  length = 13
FEATURE                 Location/Qualifiers
source                  1..13
                        mol_type = protein
                        organism = synthetic construct
SEQUENCE: 77
DTKKKPKPSN RDG                                                              13

SEQ ID NO: 78           moltype = AA  length = 12
FEATURE                 Location/Qualifiers
source                  1..12
                        mol_type = protein
                        organism = synthetic construct
SEQUENCE: 78
TKKKPKPSNR DG                                                               12

SEQ ID NO: 79           moltype = AA  length = 11
FEATURE                 Location/Qualifiers
source                  1..11
                        mol_type = protein
                        organism = synthetic construct
SEQUENCE: 79
KKKPKPSNRD G                                                                11

SEQ ID NO: 80           moltype = AA  length = 10
FEATURE                 Location/Qualifiers
source                  1..10
                        mol_type = protein
                        organism = synthetic construct
SEQUENCE: 80
KKPKPSNRDG                                                                  10

SEQ ID NO: 81           moltype = AA  length = 17
FEATURE                 Location/Qualifiers
source                  1..17
                        mol_type = protein
                        organism = synthetic construct
SEQUENCE: 81
SVKKKDTKKK PKPSNRD                                                          17

SEQ ID NO: 82           moltype = AA  length = 16
FEATURE                 Location/Qualifiers
source                  1..16
                        mol_type = protein
                        organism = synthetic construct
SEQUENCE: 82
VKKKDTKKKP KPSNRD                                                           16

SEQ ID NO: 83           moltype = AA  length = 15
FEATURE                 Location/Qualifiers
source                  1..15
                        mol_type = protein
                        organism = synthetic construct
SEQUENCE: 83
KKKDTKKKPK PSNRD                                                            15
```

-continued

| | | |
|---|---|---|
| SEQ ID NO: 84<br>FEATURE<br>source | moltype = AA   length = 14<br>Location/Qualifiers<br>1..14<br>mol_type = protein<br>organism = synthetic construct | |
| SEQUENCE: 84<br>KKDTKKKPKP SNRD | | 14 |
| SEQ ID NO: 85<br>FEATURE<br>source | moltype = AA   length = 13<br>Location/Qualifiers<br>1..13<br>mol_type = protein<br>organism = synthetic construct | |
| SEQUENCE: 85<br>KDTKKKPKPS NRD | | 13 |
| SEQ ID NO: 86<br>FEATURE<br>source | moltype = AA   length = 12<br>Location/Qualifiers<br>1..12<br>mol_type = protein<br>organism = synthetic construct | |
| SEQUENCE: 86<br>DTKKKPKPSN RD | | 12 |
| SEQ ID NO: 87<br>FEATURE<br>source | moltype = AA   length = 11<br>Location/Qualifiers<br>1..11<br>mol_type = protein<br>organism = synthetic construct | |
| SEQUENCE: 87<br>TKKKPKPSNR D | | 11 |
| SEQ ID NO: 88<br>FEATURE<br>source | moltype = AA   length = 10<br>Location/Qualifiers<br>1..10<br>mol_type = protein<br>organism = synthetic construct | |
| SEQUENCE: 88<br>KKKPKPSNRD | | 10 |
| SEQ ID NO: 89<br>FEATURE<br>source | moltype = AA   length = 16<br>Location/Qualifiers<br>1..16<br>mol_type = protein<br>organism = synthetic construct | |
| SEQUENCE: 89<br>SVKKKDTKKK PKPSNR | | 16 |
| SEQ ID NO: 90<br>FEATURE<br>source | moltype = AA   length = 15<br>Location/Qualifiers<br>1..15<br>mol_type = protein<br>organism = synthetic construct | |
| SEQUENCE: 90<br>VKKKDTKKKP KPSNR | | 15 |
| SEQ ID NO: 91<br>FEATURE<br>source | moltype = AA   length = 14<br>Location/Qualifiers<br>1..14<br>mol_type = protein<br>organism = synthetic construct | |
| SEQUENCE: 91<br>KKKDTKKKPK PSNR | | 14 |
| SEQ ID NO: 92<br>FEATURE<br>source | moltype = AA   length = 13<br>Location/Qualifiers<br>1..13<br>mol_type = protein<br>organism = synthetic construct | |
| SEQUENCE: 92<br>KKDTKKKPKP SNR | | 13 |
| SEQ ID NO: 93<br>FEATURE<br>source | moltype = AA   length = 12<br>Location/Qualifiers<br>1..12<br>mol_type = protein<br>organism = synthetic construct | |
| SEQUENCE: 93<br>KDTKKKPKPS NR | | 12 |

```
SEQ ID NO: 94              moltype = AA   length = 11
FEATURE                    Location/Qualifiers
source                     1..11
                           mol_type = protein
                           organism = synthetic construct
SEQUENCE: 94
DTKKKPKPSN R                                                         11

SEQ ID NO: 95              moltype = AA   length = 10
FEATURE                    Location/Qualifiers
source                     1..10
                           mol_type = protein
                           organism = synthetic construct
SEQUENCE: 95
TKKKPKPSNR                                                           10

SEQ ID NO: 96              moltype = AA   length = 15
FEATURE                    Location/Qualifiers
source                     1..15
                           mol_type = protein
                           organism = synthetic construct
SEQUENCE: 96
SVKKKDTKKK PKPSN                                                     15

SEQ ID NO: 97              moltype = AA   length = 14
FEATURE                    Location/Qualifiers
source                     1..14
                           mol_type = protein
                           organism = synthetic construct
SEQUENCE: 97
VKKKDTKKKP KPSN                                                      14

SEQ ID NO: 98              moltype = AA   length = 13
FEATURE                    Location/Qualifiers
source                     1..13
                           mol_type = protein
                           organism = synthetic construct
SEQUENCE: 98
KKKDTKKKPK PSN                                                       13

SEQ ID NO: 99              moltype = AA   length = 12
FEATURE                    Location/Qualifiers
source                     1..12
                           mol_type = protein
                           organism = synthetic construct
SEQUENCE: 99
KKDTKKKPKP SN                                                        12

SEQ ID NO: 100             moltype = AA   length = 11
FEATURE                    Location/Qualifiers
source                     1..11
                           mol_type = protein
                           organism = synthetic construct
SEQUENCE: 100
KDTKKKPKPS N                                                         11

SEQ ID NO: 101             moltype = AA   length = 10
FEATURE                    Location/Qualifiers
source                     1..10
                           mol_type = protein
                           organism = synthetic construct
SEQUENCE: 101
DTKKKPKPSN                                                           10

SEQ ID NO: 102             moltype = AA   length = 14
FEATURE                    Location/Qualifiers
source                     1..14
                           mol_type = protein
                           organism = synthetic construct
SEQUENCE: 102
SVKKKDTKKK PKPS                                                      14

SEQ ID NO: 103             moltype = AA   length = 13
FEATURE                    Location/Qualifiers
source                     1..13
                           mol_type = protein
                           organism = synthetic construct
SEQUENCE: 103
```

```
VKKKDTKKKP KPS                                                              13

SEQ ID NO: 104           moltype = AA   length = 12
FEATURE                  Location/Qualifiers
source                   1..12
                         mol_type = protein
                         organism = synthetic construct SEQUENCE: 104
KKKDTKKKPK PS                                                               12

SEQ ID NO: 105           moltype = AA   length = 11
FEATURE                  Location/Qualifiers
source                   1..11
                         mol_type = protein
                         organism = synthetic construct SEQUENCE: 105
KKDTKKKPKP S                                                                11

SEQ ID NO: 106           moltype = AA   length = 10
FEATURE                  Location/Qualifiers
source                   1..10
                         mol_type = protein
                         organism = synthetic construct SEQUENCE: 106
KDTKKKPKPS                                                                  10

SEQ ID NO: 107           moltype = AA   length = 13
FEATURE                  Location/Qualifiers
source                   1..13
                         mol_type = protein
                         organism = synthetic construct SEQUENCE: 107
SVKKKDTKKK PKP                                                              13

SEQ ID NO: 108           moltype = AA   length = 12
FEATURE                  Location/Qualifiers
source                   1..12
                         mol_type = protein
                         organism = synthetic construct SEQUENCE: 108
VKKKDTKKKP KP                                                               12

SEQ ID NO: 109           moltype = AA   length = 11
FEATURE                  Location/Qualifiers
source                   1..11
                         mol_type = protein
                         organism = synthetic construct SEQUENCE: 109
KKKDTKKKPK P                                                                11

SEQ ID NO: 110           moltype = AA   length = 10
FEATURE                  Location/Qualifiers
source                   1..10
                         mol_type = protein
                         organism = synthetic construct SEQUENCE: 110
KKDTKKKPKP                                                                  10

SEQ ID NO: 111           moltype = AA   length = 12
FEATURE                  Location/Qualifiers
source                   1..12
                         mol_type = protein
                         organism = synthetic construct SEQUENCE: 111
SVKKKDTKKK PK                                                               12

SEQ ID NO: 112           moltype = AA   length = 11
FEATURE                  Location/Qualifiers
source                   1..11
                         mol_type = protein
                         organism = synthetic construct SEQUENCE: 112
VKKKDTKKKP K                                                                11

SEQ ID NO: 113           moltype = AA   length = 10
FEATURE                  Location/Qualifiers
source                   1..10
                         mol_type = protein
                         organism = synthetic construct
```

```
SEQUENCE: 113
KKKDTKKKPK                                                                                    10

SEQ ID NO: 114          moltype = AA  length = 11
FEATURE                 Location/Qualifiers
source                  1..11
                        mol_type = protein
                        organism = synthetic construct
SEQUENCE: 114
SVKKKDTKKK P                                                                                  11

SEQ ID NO: 115          moltype = AA  length = 10
FEATURE                 Location/Qualifiers
source                  1..10
                        mol_type = protein
                        organism = synthetic construct
SEQUENCE: 115
VKKKDTKKKP                                                                                    10

SEQ ID NO: 116          moltype = AA  length = 10
FEATURE                 Location/Qualifiers
source                  1..10
                        mol_type = protein
                        organism = synthetic construct
SEQUENCE: 116
SVKKKDTKKK                                                                                    10

SEQ ID NO: 117          moltype = AA  length = 13
FEATURE                 Location/Qualifiers
source                  1..13
                        mol_type = protein
                        organism = synthetic construct
SEQUENCE: 117
KAGGTVTPTP NTG                                                                                13

SEQ ID NO: 118          moltype = AA  length = 12
FEATURE                 Location/Qualifiers
source                  1..12
                        mol_type = protein
                        organism = synthetic construct
SEQUENCE: 118
KAGGTVTPTP NT                                                                                 12

SEQ ID NO: 119          moltype = AA  length = 11
FEATURE                 Location/Qualifiers
source                  1..11
                        mol_type = protein
                        organism = synthetic construct
SEQUENCE: 119
KAGGTVTPTP N                                                                                  11

SEQ ID NO: 120          moltype = AA  length = 10
FEATURE                 Location/Qualifiers
source                  1..10
                        mol_type = protein
                        organism = synthetic construct
SEQUENCE: 120
KAGGTVTPTP                                                                                    10

SEQ ID NO: 121          moltype = AA  length = 9
FEATURE                 Location/Qualifiers
source                  1..9
                        mol_type = protein
                        organism = synthetic construct
SEQUENCE: 121
KAGGTVTPT                                                                                      9

SEQ ID NO: 122          moltype = AA  length = 8
FEATURE                 Location/Qualifiers
source                  1..8
                        mol_type = protein
                        organism = synthetic construct
SEQUENCE: 122
KAGGTVTP                                                                                       8

SEQ ID NO: 123          moltype = AA  length = 7
FEATURE                 Location/Qualifiers
source                  1..7
                        mol_type = protein
```

```
                                    -continued

SEQUENCE: 123
KAGGTVT                                                                    7

SEQ ID NO: 124          moltype = AA   length = 6
FEATURE                 Location/Qualifiers
source                  1..6
                        mol_type = protein
                        organism = synthetic construct
SEQUENCE: 124
KAGGTV                                                                     6

SEQ ID NO: 125          moltype = AA   length = 5
FEATURE                 Location/Qualifiers
source                  1..5
                        mol_type = protein
                        organism = synthetic construct
SEQUENCE: 125
KAGGT                                                                      5

SEQ ID NO: 126          moltype = AA   length = 12
FEATURE                 Location/Qualifiers
source                  1..12
                        mol_type = protein
                        organism = synthetic construct
SEQUENCE: 126
AGGTVTPTPN TG                                                             12

SEQ ID NO: 127          moltype = AA   length = 11
FEATURE                 Location/Qualifiers
source                  1..11
                        mol_type = protein
                        organism = synthetic construct
SEQUENCE: 127
AGGTVTPTPN T                                                              11

SEQ ID NO: 128          moltype = AA   length = 10
FEATURE                 Location/Qualifiers
source                  1..10
                        mol_type = protein
                        organism = synthetic construct
SEQUENCE: 128
AGGTVTPTPN                                                                10

SEQ ID NO: 129          moltype = AA   length = 9
FEATURE                 Location/Qualifiers
source                  1..9
                        mol_type = protein
                        organism = synthetic construct
SEQUENCE: 129
AGGTVTPTP                                                                  9

SEQ ID NO: 130          moltype = AA   length = 8
FEATURE                 Location/Qualifiers
source                  1..8
                        mol_type = protein
                        organism = synthetic construct
SEQUENCE: 130
AGGTVTPT                                                                   8

SEQ ID NO: 131          moltype = AA   length = 7
FEATURE                 Location/Qualifiers
source                  1..7
                        mol_type = protein
                        organism = synthetic construct
SEQUENCE: 131
AGGTVTP                                                                    7

SEQ ID NO: 132          moltype = AA   length = 6
FEATURE                 Location/Qualifiers
source                  1..6
                        mol_type = protein
                        organism = synthetic construct
SEQUENCE: 132
AGGTVT                                                                     6

SEQ ID NO: 133          moltype = AA   length = 5
FEATURE                 Location/Qualifiers
source                  1..5
```

```
                                    mol_type = protein
                                    organism = synthetic construct
SEQUENCE: 133
AGGTV                                                                              5

SEQ ID NO: 134              moltype = AA   length = 11
FEATURE                     Location/Qualifiers
source                      1..11
                            mol_type = protein
                            organism = synthetic construct
SEQUENCE: 134
GGTVTPTPNT G                                                                      11

SEQ ID NO: 135              moltype = AA   length = 10
FEATURE                     Location/Qualifiers
source                      1..10
                            mol_type = protein
                            organism = synthetic construct
SEQUENCE: 135
GGTVTPTPNT                                                                        10

SEQ ID NO: 136              moltype = AA   length = 9
FEATURE                     Location/Qualifiers
source                      1..9
                            mol_type = protein
                            organism = synthetic construct
SEQUENCE: 136
GGTVTPTPN                                                                          9

SEQ ID NO: 137              moltype = AA   length = 8
FEATURE                     Location/Qualifiers
source                      1..8
                            mol_type = protein
                            organism = synthetic construct
SEQUENCE: 137
GGTVTPTP                                                                           8

SEQ ID NO: 138              moltype = AA   length = 7
FEATURE                     Location/Qualifiers
source                      1..7
                            mol_type = protein
                            organism = synthetic construct
SEQUENCE: 138
GGTVTPT                                                                            7

SEQ ID NO: 139              moltype = AA   length = 6
FEATURE                     Location/Qualifiers
source                      1..6
                            mol_type = protein
                            organism = synthetic construct
SEQUENCE: 139
GGTVTP                                                                             6

SEQ ID NO: 140              moltype = AA   length = 5
FEATURE                     Location/Qualifiers
source                      1..5
                            mol_type = protein
                            organism = synthetic construct
SEQUENCE: 140
GGTVT                                                                              5

SEQ ID NO: 141              moltype = AA   length = 10
FEATURE                     Location/Qualifiers
source                      1..10
                            mol_type = protein
                            organism = synthetic construct
SEQUENCE: 141
GTVTPTPNTG                                                                        10

SEQ ID NO: 142              moltype = AA   length = 9
FEATURE                     Location/Qualifiers
source                      1..9
                            mol_type = protein
                            organism = synthetic construct
SEQUENCE: 142
GTVTPTPNT                                                                          9

SEQ ID NO: 143              moltype = AA   length = 8
FEATURE                     Location/Qualifiers
```

| | | |
|---|---|---|
| source | 1..8<br>mol_type = protein<br>organism = synthetic construct | |
| SEQUENCE: 143<br>GTVTPTPN | | 8 |
| SEQ ID NO: 144<br>FEATURE<br>source | moltype = AA length = 7<br>Location/Qualifiers<br>1..7<br>mol_type = protein<br>organism = synthetic construct | |
| SEQUENCE: 144<br>GTVTPTP | | 7 |
| SEQ ID NO: 145<br>FEATURE<br>source | moltype = AA length = 6<br>Location/Qualifiers<br>1..6<br>mol_type = protein<br>organism = synthetic construct | |
| SEQUENCE: 145<br>GTVTPT | | 6 |
| SEQ ID NO: 146<br>FEATURE<br>source | moltype = AA length = 5<br>Location/Qualifiers<br>1..5<br>mol_type = protein<br>organism = synthetic construct | |
| SEQUENCE: 146<br>GTVTP | | 5 |
| SEQ ID NO: 147<br>FEATURE<br>source | moltype = AA length = 9<br>Location/Qualifiers<br>1..9<br>mol_type = protein<br>organism = synthetic construct | |
| SEQUENCE: 147<br>TVTPTPNTG | | 9 |
| SEQ ID NO: 148<br>FEATURE<br>source | moltype = AA length = 8<br>Location/Qualifiers<br>1..8<br>mol_type = protein<br>organism = synthetic construct | |
| SEQUENCE: 148<br>TVTPTPNT | | 8 |
| SEQ ID NO: 149<br>FEATURE<br>source | moltype = AA length = 7<br>Location/Qualifiers<br>1..7<br>mol_type = protein<br>organism = synthetic construct | |
| SEQUENCE: 149<br>TVTPTPN | | 7 |
| SEQ ID NO: 150<br>FEATURE<br>source | moltype = AA length = 6<br>Location/Qualifiers<br>1..6<br>mol_type = protein<br>organism = synthetic construct | |
| SEQUENCE: 150<br>TVTPTP | | 6 |
| SEQ ID NO: 151<br>FEATURE<br>source | moltype = AA length = 5<br>Location/Qualifiers<br>1..5<br>mol_type = protein<br>organism = synthetic construct | |
| SEQUENCE: 151<br>TVTPT | | 5 |
| SEQ ID NO: 152<br>FEATURE<br>source | moltype = AA length = 8<br>Location/Qualifiers<br>1..8<br>mol_type = protein<br>organism = synthetic construct | |
| SEQUENCE: 152<br>VTPTPNTG | | 8 |
| SEQ ID NO: 153 | moltype = AA length = 7 | |

```
FEATURE                 Location/Qualifiers
source                  1..7
                        mol_type = protein
                        organism = synthetic construct
SEQUENCE: 153
VTPTPNT                                                                          7

SEQ ID NO: 154          moltype = AA   length = 6
FEATURE                 Location/Qualifiers
source                  1..6
                        mol_type = protein
                        organism = synthetic construct
SEQUENCE: 154
VTPTPN                                                                           6

SEQ ID NO: 155          moltype = AA   length = 5
FEATURE                 Location/Qualifiers
source                  1..5
                        mol_type = protein
                        organism = synthetic construct
SEQUENCE: 155
VTPTP                                                                            5

SEQ ID NO: 156          moltype = AA   length = 7
FEATURE                 Location/Qualifiers
source                  1..7
                        mol_type = protein
                        organism = synthetic construct
SEQUENCE: 156
TPTPNTG                                                                          7

SEQ ID NO: 157          moltype = AA   length = 6
FEATURE                 Location/Qualifiers
source                  1..6
                        mol_type = protein
                        organism = synthetic construct
SEQUENCE: 157
TPTPNT                                                                           6

SEQ ID NO: 158          moltype = AA   length = 5
FEATURE                 Location/Qualifiers
source                  1..5
                        mol_type = protein
                        organism = synthetic construct
SEQUENCE: 158
TPTPN                                                                            5

SEQ ID NO: 159          moltype = AA   length = 6
FEATURE                 Location/Qualifiers
source                  1..6
                        mol_type = protein
                        organism = synthetic construct
SEQUENCE: 159
PTPNTG                                                                           6

SEQ ID NO: 160          moltype = AA   length = 5
FEATURE                 Location/Qualifiers
source                  1..5
                        mol_type = protein
                        organism = synthetic construct
SEQUENCE: 160
PTPNT                                                                            5

SEQ ID NO: 161          moltype = AA   length = 5
FEATURE                 Location/Qualifiers
source                  1..5
                        mol_type = protein
                        organism = synthetic construct
SEQUENCE: 161
TPNTG                                                                            5
```

The invention claimed is:

1. An endolysin polypeptide that has lytic activity for *Staphylococcus*, said endolysin polypeptide comprising a polypeptide, wherein the amino acid sequence of the polypeptide has at least 98% sequence identity with SEQ ID NO: 1; wherein the endolysin polypeptide has enhanced lytic activity for *Staphylococcus* in human serum compared to:
the endolysin with the amino acid sequence as set forward in SEQ ID NO: 2, and/or
the endolysin with the amino acid sequence as set forward in SEQ ID NO: 3; and
wherein the M23 endopeptidase domain and the CHAP domain in the endolysin polypeptide are separated by a linker that comprises at least 13 amino acids.

2. The endolysin polypeptide according to claim 1, wherein the amino acid sequence of the endolysin polypeptide has at least 99% sequence identity with SEQ ID NO: 1.

3. A composition comprising the endolysin polypeptide according to claim 1.

4. The composition according to claim 3, further comprising an excipient acceptable for cosmetics.

5. The composition according to claim 3, further comprising a pharmaceutically acceptable excipient.

6. The composition according to claim 3, further comprising an additional active ingredient.

7. A method of treatment of a condition associated with infection with a *Staphylococcus*, comprising administration an endolysin polypeptide according to claim 1.

8. The method of treatment according to claim 7, wherein the condition to be treated is selected from: a skin infection, soft tissue infections, infected diabetic foot ulcers, mastitis, pneumonia, meningitis, endocarditis, Toxic Shock Syndrome (TSS), sepsis, septicaemia, bacteraemia, or osteomyelitis.

9. The method of treatment according to claim 8, wherein the skin infection is selected from the group consisting of pimples, impetigo, boils, furuncles, cellulitis, folliculitis, carbuncles, scaled skin syndrome, atopic dermatitis, and abscesses.

10. The method of treatment according to claim 7, wherein the condition to be treated is selected from the group consisting of bacteraemia, infective endocarditis, prosthetic joint infection, osteomyelitis, indwelling medical device infection and implanted medical device infection.

11. The endolysin polypeptide comprising a polypeptide according to claim 1, wherein the polypeptide has 100% sequence identity with SEQ ID NO: 1.

* * * * *